US009414943B2

(12) United States Patent
Mangiardi et al.

(10) Patent No.: US 9,414,943 B2
(45) Date of Patent: Aug. 16, 2016

(54) IMPLANTATION SYSTEM WITH HANDLE AND CATHETER AND METHOD OF USE THEREOF

(71) Applicant: QUALIMED INNOVATIVE MEDIZINPRODUKTE GMBH, Winsen (Luhe) (DE)

(72) Inventors: Eric K. Mangiardi, Charlotte, NC (US); Martina Schmitt, Winsen (Luhe) (DE)

(73) Assignee: QUALIMED INNOVATIVE MEDIZINPRODUKTE GMBH, Winsen (Luhe) (DE)

( * ) Notice: Subject to any disclaimer, the term of this patent is extended or adjusted under 35 U.S.C. 154(b) by 171 days.

(21) Appl. No.: 13/952,334

(22) Filed: Jul. 26, 2013

(65) Prior Publication Data

US 2013/0310915 A1    Nov. 21, 2013

Related U.S. Application Data

(63) Continuation of application No. 13/486,249, filed on Jun. 1, 2012, and a continuation-in-part of application No. 12/545,982, filed on Aug. 24, 2009.

(51) Int. Cl.
*A61F 11/00* (2006.01)
*A61F 2/95* (2013.01)
(Continued)

(52) U.S. Cl.
CPC . *A61F 2/95* (2013.01); *A61F 2/958* (2013.01); *A61F 2/966* (2013.01); *A61B 17/2841* (2013.01); *A61B 2017/1205* (2013.01);
(Continued)

(58) Field of Classification Search
CPC ........... A61F 2/958; A61F 2/95; A61F 2/966; A61F 2002/9517; A61B 2090/0811; A61B 2090/061; A61B 17/2841; A61M 25/0136; A61M 25/0068; A61M 25/0662
USPC ............. 606/108; 604/131, 151, 155, 164.04, 604/164.07
See application file for complete search history.

(56) References Cited

U.S. PATENT DOCUMENTS 5,201,757 A * 4/1993 Heyn ........................ A61F 2/95
606/198
5,308,342 A * 5/1994 Sepetka ............ A61M 25/0054
604/264

(Continued)

FOREIGN PATENT DOCUMENTS

CN       2652421 Y    11/2004
CN       1961847 A     5/2007

(Continued)

OTHER PUBLICATIONS

International Search Report and Written Opinion of the International Searching Authority issued in International Patent Application No. PCT/US2012/040453 and mailed on Dec. 14, 2012.

(Continued)

*Primary Examiner* — Richard Louis
(74) *Attorney, Agent, or Firm* — Ping Wang; Andrews Kurth LLP

(57) ABSTRACT

A system for deploying an implantable medical device into a body lumen is disclosed. The system comprises a catheter having functional zones for stability, protection, flexibility, trackability and pushability. The system further comprises a device for deploying an implantable medical device with the catheter. A method for deploying an implantable medical device into a body lumen using the system is also disclosed.

21 Claims, 21 Drawing Sheets

(51) Int. Cl.
  *A61F 2/966* (2013.01)
  *A61F 2/958* (2013.01)
  *A61B 17/28* (2006.01)
  *A61B 17/12* (2006.01)
  *A61M 25/00* (2006.01)
  *A61M 25/01* (2006.01)
  *A61M 25/06* (2006.01)

(52) U.S. Cl.
  CPC .. *A61B 2090/061* (2016.02); *A61B 2090/0811* (2016.02); *A61F 2002/9517* (2013.01); *A61M 25/0068* (2013.01); *A61M 25/0136* (2013.01); *A61M 25/0662* (2013.01)

(56) References Cited

U.S. PATENT DOCUMENTS

| | | | |
|---|---|---|---|
| 5,370,134 A | | 12/1994 | Chin et al. |
| 5,395,334 A | * | 3/1995 | Keith ................ A61M 25/0662 604/103.09 |
| 5,571,168 A | | 11/1996 | Toro |
| 5,891,112 A | | 4/1999 | Samson |
| 5,968,052 A | | 10/1999 | Sullivan et al. |
| 6,077,258 A | | 6/2000 | Lange et al. |
| 6,143,021 A | | 11/2000 | Staehle |
| 6,254,588 B1 | * | 7/2001 | Jones ................ A61M 25/0012 604/525 |
| 6,383,211 B1 | * | 5/2002 | Staehle ................ A61F 2/95 606/108 |
| 6,413,269 B1 | | 7/2002 | Bui et al. |
| 6,530,933 B1 | | 3/2003 | Yeung et al. |
| 6,631,715 B2 | | 10/2003 | Kirn |
| 7,527,644 B2 | | 5/2009 | Mangiardi et al. |
| 7,547,321 B2 | | 6/2009 | Silvestri et al. |
| 2004/0153137 A1 | | 8/2004 | Gaschino et al. |
| 2005/0038495 A1 | | 2/2005 | Greenan |
| 2005/0096664 A1 | * | 5/2005 | Cohn ................ A61B 17/22031 606/108 |
| 2005/0171591 A1 | * | 8/2005 | McHale ................ A61F 2/958 623/1.11 |
| 2006/0184224 A1 | * | 8/2006 | Angel ................ A61F 2/95 623/1.11 |
| 2007/0073247 A1 | | 3/2007 | Ewaschuk |
| 2007/0179586 A1 | | 8/2007 | Aguirre et al. |
| 2007/0233222 A1 | | 10/2007 | Roeder et al. |
| 2007/0250150 A1 | | 10/2007 | Pal et al. |
| 2008/0228258 A1 | * | 9/2008 | Gerdts et al. ................ 623/1.11 |
| 2008/0269868 A1 | * | 10/2008 | Bei ................ A61F 2/013 623/1.11 |
| 2009/0118740 A1 | | 5/2009 | Mangiardi et al. |
| 2011/0046710 A1 | | 2/2011 | Mangiardi et al. |

FOREIGN PATENT DOCUMENTS

| | | |
|---|---|---|
| WO | 02083037 | 10/2002 |
| WO | 2006072934 | 7/2006 |
| WO | 2011028302 A1 | 3/2011 |

OTHER PUBLICATIONS

International Search Report and Written Opinion of the International Searching Authority issued in International Patent Application No. PCT/US2010/029218 and mailed on Jan. 25, 2011.
File history of U.S. Appl. No. 12/545,982, filed on Aug. 24, 2009.
File history of U.S. Appl. No. 13/486,249, filed on Jun. 1, 2012.

* cited by examiner

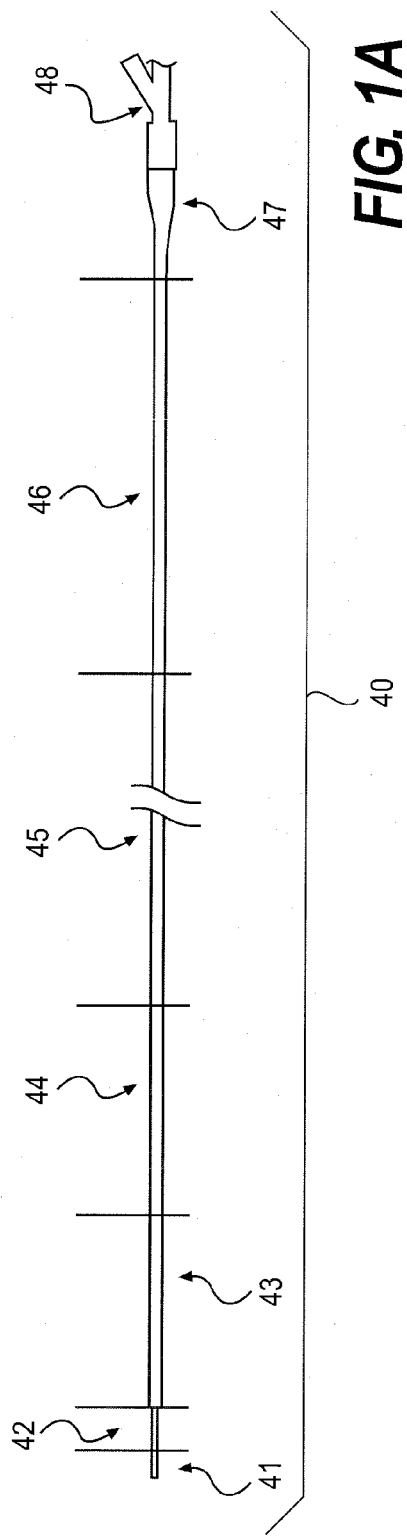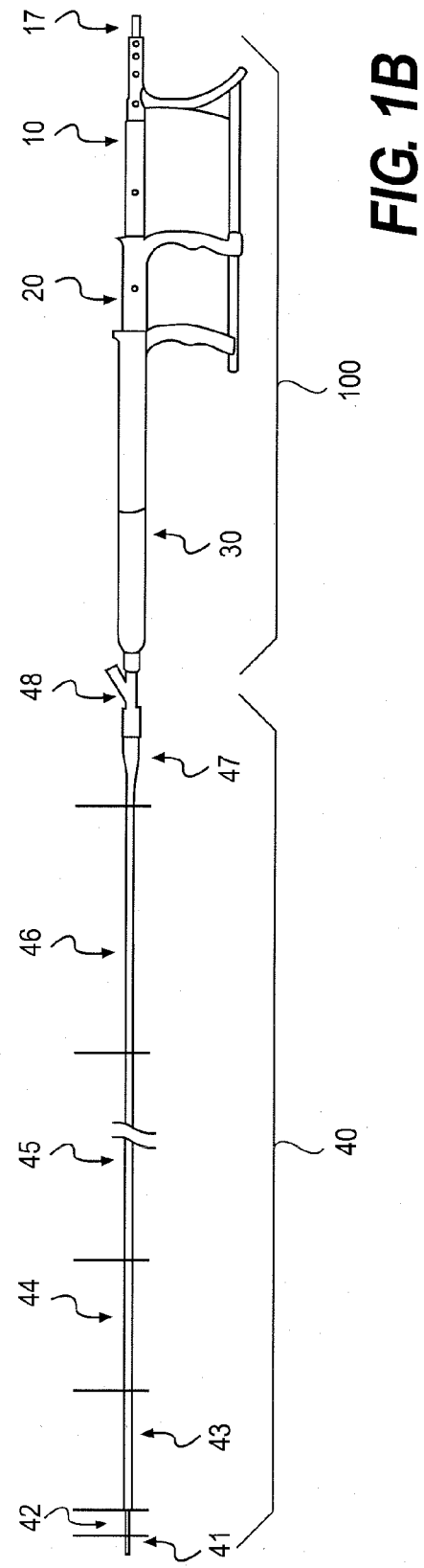

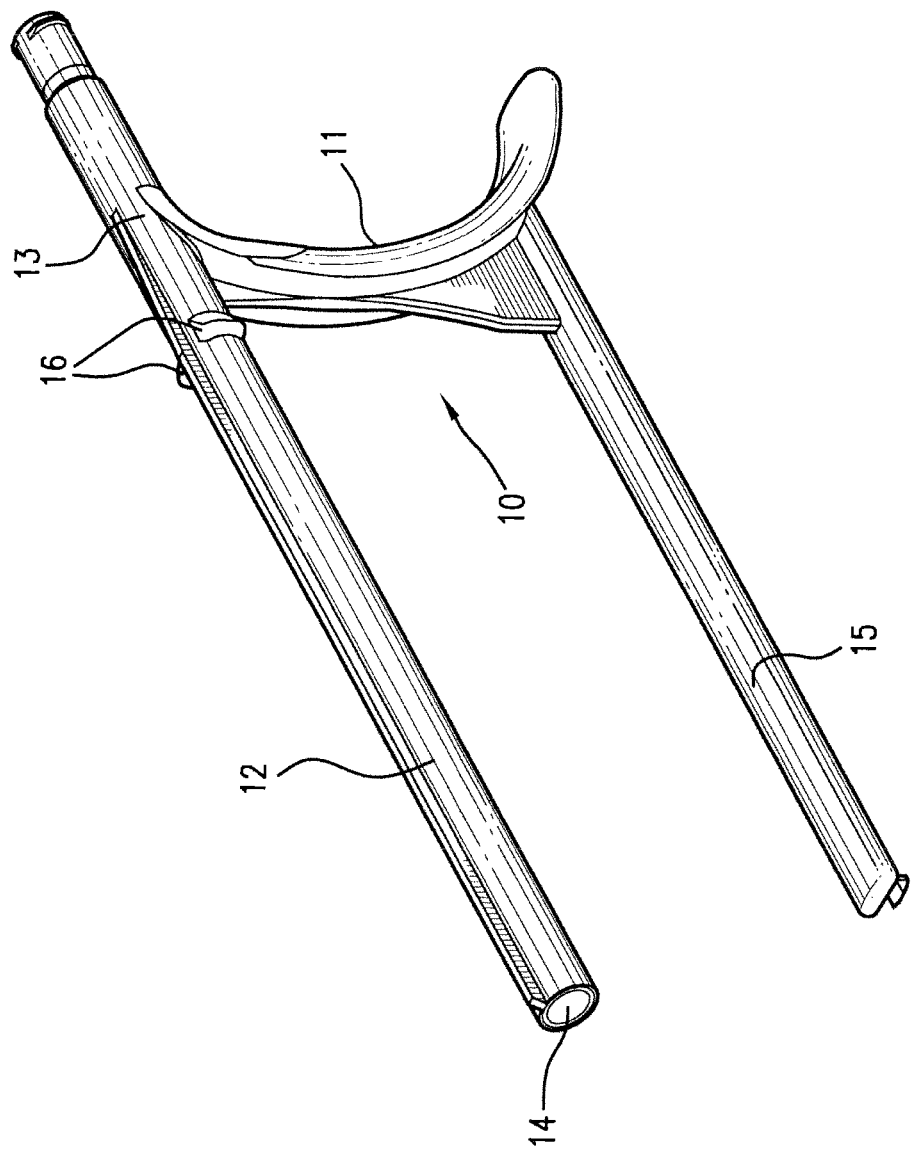

IMPLANTATION SYSTEM WITH HANDLE AND CATHETER AND METHOD OF USE THEREOF

This application is a Continuation of application Ser. No. 13/486,249, filed on Jun. 1, 2012, which is a Continuation-In-Part of U.S. patent application Ser. No. 12/545,982, filed on Aug. 24, 2009. The entirety of the aforementioned applications is incorporated herein by reference.

FIELD

The present application relates generally to medical devices and, in particular, to a delivery system and method for introducing implantable medical devices into a body cavity.

BACKGROUND

Implants may be placed in the human body for a variety of reasons. For example, stents are placed in a number of different body lumens such as blood vessels and biliary ducts; vena cava filters are implanted in the vena cava to catch thrombus sloughed off from other sites within the body; and vaso-occlusive devices are used for the treatment of intravascular aneurysms.

Interventional practitioners, regardless of subspecialty, have always had to demonstrate profound dexterity in order to effectively and accurately perform invasive procedures. This is particularly the case with the delivery and deployment of implantable devices where there is very little room for error with respect to placement. In order to assist with placement accuracy, many interventionalists utilize scopes, such as bronchoscopes or endoscopes, ultrasound, ct scanning, or other imaging modalities as well as various supporting instruments, guiding catheters, introducers, and other such devices during various diagnostic and interventional procedures. However, handling the imaging modality, introduction, and access equipment, and the delivery catheter can often be a clumsy process when using multiple devices especially where by the two devices easily disassociate from each other. Moreover, since many delivery catheters, for one reason or another, cannot be adequately managed with one hand, additional personnel are required when handling the scope and the delivery catheter.

Therefore, there is an existing need for a delivery system that allows a physician to deploy an implantable device with one hand.

SUMMARY

One aspect of the present application relates to a catheter for deploying an implantable medical device. The catheter comprises an elongated body having a distal end and a proximate end. The elongated body further comprises a stabilization zone at the distal end, a protection zone located between the stabilization zone and the proximate end, a flexibility zone located between the protection zone and the proximate end, a trackability zone located between the flexibility zone and the proximate end; a pushability zone located between the trackability zone and the proximate end, and a connector at the proximate end for connecting to a deployment device, wherein the protection zone is adapted to carry an implantable device and wherein the stabilization zone and protection zone have a flexibility index of less than 3000 mN, the flexibility zone has a flexibility index of less than 3500 mN, the trackability zone has a flexibility index of less than 4500 mN, and the pushability zone has a flexibility index of less than 6000 mN.

Another aspect of the present application relates to a method for deploying an implantable medical device comprising: advancing the catheter for deploying an implantable medical device, the catheter having a tip at its distal end and a connector at its proximate end and comprising a stabilization zone proximate to the tip, a protection zone proximate to the stabilization zone, a flexibility zone proximate to the protection zone, a pushability zone proximate to the trackability zone and a strain relief area between the flexibility zone and the connector into a body lumen, wherein an implantable medical device affixed to the protection zone of said catheter, attaching the proximal end of the catheter to an advancing device, the advancing device comprising: a base member comprising a base handle; and a deployment extension having a distal end and a proximate end, the proximate end is connected to the base handle; a first tubular member that fits over the deployment extension and is longitudinally slidable over the deployment extension, the first tubular member comprising: a first tubular body with a distal end and a proximal end; and a first handle for controlling movement of the first tubular member; and a second tubular member that fits over the first tubular member and is longitudinally slidable over the first tubular member, the second tubular member comprising: a second tubular body with a distal end and a proximal end; and a second handle for controlling movement of the second tubular member, wherein the first handle is located between the base handle and the second handle and wherein the distal ends of the deployment extension, the first tubular body, and the second tubular body are adapted to deploy an implantable medical device, and retracting the first tubular member and the second tubular member towards the base member to deploy the implantable medical device in the body lumen.

Another aspect of the present application relates to a kit comprising: a catheter for deploying an implantable medical device, the catheter having a tip at its distal end and a connector at its proximate end and comprising a stabilization zone proximate to the tip, a protection zone proximate to the stabilization zone, a flexibility zone proximate to the protection zone, a pushability zone proximate to the flexibility zone and a strain relief area between the pushability zone and the connector, and an advancing device, the advancing device comprising: a base member comprising a base handle; and a deployment extension having a distal end and a proximate end, the proximate end is connected to the base handle; a first tubular member that fits over the deployment extension and is longitudinally slidable over the deployment extension, the first tubular member comprising: a first tubular body with a distal end and a proximal end; and a first handle for controlling movement of the first tubular member; and a second tubular member that fits over the first tubular member and is longitudinally slidable over the first tubular member, the second tubular member comprising: a second tubular body with a distal end and a proximal end; and a second handle for controlling movement of the second tubular member, wherein the first handle is located between the base handle and the second handle and wherein the distal ends of the deployment extension, the first tubular body, and the second tubular body are adapted to deploy an implantable medical device.

Further objectives, features and advantages of the invention will be apparent from the following detailed description taken in conjunction with the accompanying drawings.

BRIEF DESCRIPTION OF THE DRAWINGS

For the purposes of this disclosure, unless otherwise indicated, identical reference numerals used in different figures refer to the same component.

FIG. 1A shows a perspective view of an exemplary a catheter device 40 of the present application. FIG. 1B shows the catheter device 40 attached to a delivery device 100 in a pre-deployment configuration.

FIGS. 4A-4C are perspective views of an embodiment of the base member of the delivery system 100.

DETAILED DESCRIPTION

Figure 2:
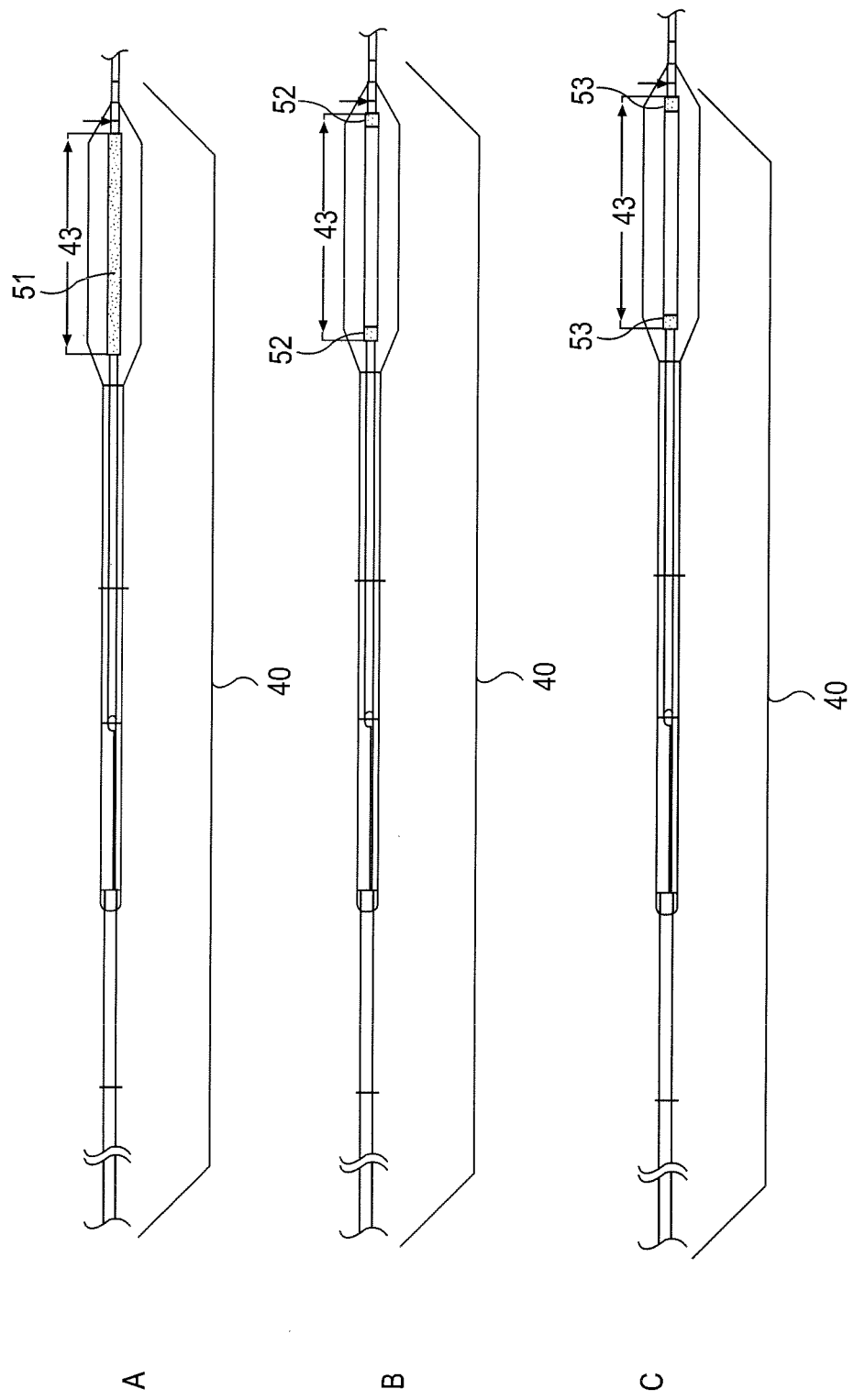
FIGS. 2A-C show a view of the catheter device 40 comprising radio opaque markers in the protection zone 43.

The following detailed description is presented to enable any person skilled in the art to make and use the invention. For purposes of explanation specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

One aspect of the present application relates to a catheter for deploying an implantable medical device. The catheter has an elongated body with a distal end and a proximate end. The elongated body comprises a stabilization zone at the distal end, a protection zone adapted to carry a medical device and located between the stabilization zone and the proximate end and is proximate to the stabilization, a flexibility zone located between the protection zone and the proximate end and is proximate to the protection zone, a trackability zone located between the flexibility zone and the proximate end and is proximate to the flexibility zone, a pushability zone located between the trackability zone and the proximate end and is proximate to the trackability zone, and a connector at the proximate end to connect the catheter to a delivery device.

Among the multiple zones of the elongated body, the stabilization and protection zones have the highest flexibility to facilitate placement of the medical device, such as a stent, carrying on the protection zone. The flexibility zone has a flexibility that equals to, or is less than, that of the stabilization and protection zones. The trackability zone has a flexibility that is less than that of the pushability zone. The pushability zone is the least flexible zone and has enough rigidity to facilitate advancement of the distal portion of the catheter body. As used herein, flexibility for each zone is determined by a 3-point bending deflection test performed according to ASTM Standards 790. The test results, expressed in the units of milli-Newton (mN), is referred to as the "flexibility index" of the tested material. In general, the higher is the flexibility index, the lower is the flexibility of the tested material.

In some embodiments, the different zones have different material compositions in order to achieve desired flexibility. In some other embodiments, zones of different flexibility are connected through transition areas. Each transition area is an area of intermediate flexibility between the adjacent zones it resides between. In some embodiments, the transition area consist of a gradual mixture of the polymer mixture of one zone into the adjacent zone, or a gradual change in the weave pattern of the polymer from one zone into the adjacent zone.

In some embodiment, the distal end of the stability zone contains a tip that allows the catheter to move through a body lumen without damaging the tissue lining of the body lumen due to the conical elongated tip made of a polyemite blend that allows for a soft flexible contour when traversing various tortuous lumens.

In some embodiments, the elongated body further contains a strain relief area between the pushability zone and the connector that reduces the pressure of the pushability zone closest to the handle to allow for the area to flex while applying significant pushing pressure thus eliminating the potential for kinking. The strain relief is made of alternating undulating open and closed levels that allow for compression and bending much like that of a standard computer cord or iron. It is more flexible than the pushability zone.

In one embodiment, the catheter further comprises an implantable medical device affixed to the protection zone. In a related embodiment, the implantable medical device is a stent.

In another embodiment, the protection zone comprises an inflatable balloon for deploying the implantable medical device.

In another embodiment, the stabilization zone is coated with or comprises an embedded radio-opaque substance.

In another embodiment, the protection zone is coated with or comprises an embedded radio-opaque substance.

In another embodiment, the flexibility zone is coated with or comprises an embedded radio-opaque substance.

In another embodiment, the trackability zone is coated with or comprises an embedded radio-opaque substance.

In another embodiment, the pushability zone is coated with or comprises an embedded radio-opaque substance.

Another aspect of the present application relates to a method for deploying an implantable medical device comprising: advancing the a catheter for deploying an implantable medical device, the catheter having a tip at its distal end and a connector at its proximate end and comprising a stabilization zone proximate to the tip, a protection zone proximate to the stabilization zone, a flexibility zone proximate to the protection zone, a pushability zone proximate to the flexibility zone and a strain relief area between the pushability zone and the connector into a body lumen, wherein an implantable medical device affixed to the protection zone of said catheter, attaching the proximal end of the catheter to an advancing device, the advancing device comprising: a base member comprising a base handle; and a deployment extension having a distal end and a proximate end, the proximate end is connected to the base handle; a first tubular member that fits over the deployment extension and is longitudinally slidable over the deployment extension, the first tubular member comprising: a first tubular body with a distal end and a proximal end; and a first handle for controlling movement of the first tubular member; and a second tubular member that fits over the first tubular member and is longitudinally slidable over the first tubular member, the second tubular member comprising: a second tubular body with a distal end and a proximal end; and a second handle for controlling movement of the second tubular member, wherein the first handle is located between the base handle and the second handle and wherein the distal ends of the deployment extension, the first tubular body, and the second tubular body are adapted to deploy an implantable medical device, and retracting the first tubular member and the second tubular member towards the base member to deploy the implantable medical device in the body lumen.

In one embodiment, the implantable medical device is a stent.

In another embodiment, the method further comprises attaching a viewing device to the base member. In a related embodiment the viewing device is an endoscope. In another related embodiment, the viewing device is a fiber optic based viewing device.

In another embodiment, the body lumen is a blood vessel or a bile duct.

Another aspect of the present application relates to a kit comprising: a catheter for deploying an implantable medical device, the catheter having a tip at its distal end and a connector at its proximate end and comprising a stabilization zone proximate to the tip, a protection zone proximate to the stabilization zone, a flexibility zone proximate to the protection zone, a pushability zone proximate to the flexibility zone and a strain relief area between the pushability zone and the connector, and an advancing device, the advancing device comprising: a base member comprising a base handle; and a deployment extension having a distal end and a proximate end, the proximate end is connected to the base handle; a first tubular member that fits over the deployment extension and is longitudinally slidable over the deployment extension, the first tubular member comprising: a first tubular body with a distal end and a proximal end; and a first handle for controlling movement of the first tubular member; and a second tubular member that fits over the first tubular member and is longitudinally slidable over the first tubular member, the second tubular member comprising: a second tubular body with a distal end and a proximal end; and a second handle for controlling movement of the second tubular member, wherein the first handle is located between the base handle and the second handle and wherein the distal ends of the deployment extension, the first tubular body, and the second tubular body are adapted to deploy an implantable medical device.

In one embodiment, the kit further comprises an implantable medical device. In a related embodiment, the implantable medical device is a stent.

In another embodiment, the kit further comprises a guidewire.

In another embodiment, the kit further comprises an introducer sheath.

In another embodiment, the kit further comprises a viewing device attachable to the base member. In a related embodiment, the viewing device is an endoscope.

FIG. 1A shows an embodiment of the catheter device 40 of the present application. The catheter device 40 comprises a tip 41 at the end of the catheter device 40 most distal to the delivery system 100. Immediately proximate to the tip 41 are functional zones of the catheter device 40 for stabilization 42, protection 43, flexibility 44, trackability 45, and pushability 46. Immediately proximate to the pushability zone 46 is a region of the catheter device 40 serving as a strain relief area 47 and a connector 48 for attaching the catheter device 40 to a delivery device 100 described herein or to some other type of medical device. FIG. 1B is a diagram showing the catheter device 40 attached to the delivery device 100.

In particular embodiments, the diameters of the zones of the catheter may be the same as one another or different. In particular embodiments, the durometer, or hardness, of the different zones may be the same as one another or different. In particular embodiments, the different zones may be made of the same material, or from different materials. In particular embodiments, a zone of the catheter may comprise a material selected from a nylon, PEBAX (polyether block amide; Arkema, Columbes, France), a polyether block amide that is free of plasticizers, a polyamide, polyetheretherketone (PEEK), any other suitable polymer material, and combinations thereof.

In a particular embodiment the distal end of the catheter device 40 comprises a tip 41 that allows the catheter to move into or through a body lumen without catching on or damaging the tissues lining said body lumen. In a further particular embodiment, the tip 41 comprises a radio-opaque substance that is visible under fluoroscopy. In a still further embodiment, the radio-opaque substance is embedded into or sealed within the tip 41. In another still further embodiment, the tip 41 is coated or painted with the radio-opaque substance.

In another particular embodiment, the catheter device 40 comprises a "stability" zone 42 immediately proximate to the distal tip 41. The stabilization zone 42 provides an area of the catheter distal to the region upon which the implantable medical device is carried that enhances the stability of the catheter during deployment of the implantable medical device in the body lumen.

In a related embodiment, the length of said stabilization zone 42 is between about 1 mm and about 7 mm. In a further embodiment, the length of said stabilization zone 42 is between about 1 mm and about 5 mm. In a still further embodiment, the length of said stabilization zone 42 is between about 2 mm and about 4 mm. In a yet still further embodiment, the length of said stabilization zone 42 is about 3 mm. In a particular embodiment, the stabilization zone 42 has a flexibility index of about 2000-4000 mN in a 3 point bending deflection test. In another embodiment, the stabilization zone 42 has a flexibility index of about less than 3000 mN in a 3-point bending deflection test. In a further embodiment, the stabilization zone 42 has a flexibility index of about 2700-3000 mN in a 3 point bending deflection test. All 3-point bending deflection tests described hereinafter are performed using the ASTM Standards 790

In a further particular embodiment, the stabilization zone 42 comprises a magnetic or ferrous material that allows the direction of the catheter to be manipulated during insertion with an externally controlled magnetic field.

In another related embodiment, the magnitude of the externally controlled magnetic field is between about 0.01 Tesla and about 0.5 Tesla. In a further embodiment, the magnitude of the externally controlled magnetic field is between about 0.05 Tesla and about 0.2 Tesla. In a still further embodiment, the magnitude of the externally controlled magnetic field is between about 0.08 Tesla and about 0.1 Tesla.

In another particular embodiment, the catheter device 40 comprises a "protection" zone 43 immediately proximate to the stabilization zone 42. The protection zone 43 comprises an area upon which an implantable medical device is emplaced for insertion and implantation in a body lumen. In a particular embodiment, the implantable medical device is a stent.

In particular embodiments, the area upon which the implantable medical device is emplaced comprises an inflatable balloon. Inflation of the balloon upon which the implantable medical device is emplaced causes the implantable medical device to expand against the walls of the body lumen. Subsequent deflation of said area leaves the implantable medical device expanded against the walls of the body lumen and dissociates the implantable medical device from the catheter in general and from the protection zone 43 in particular.

In some embodiments, as shown in FIGS. 2A-C, the protection zone further comprises at least one radio-opaque marker coated onto the catheter. In particular embodiments, the at least one radio-opaque marker is a coating of tungsten in urethane. In some embodiments, the marker is sealed by overcoating with an additional layer of urethane. In some embodiments, the at least one radio-opaque marker is an integrated tantal marker (ITM). Coating of at least one radio-opaque marker onto the protection zone 43 of the catheter 40 allows for the elimination of marker bands on the device, giving the device a lower profile and allowing more flexibility and pushability of the catheter device 40 because there are no defects in the device for the seating of markers. Additionally, the at least one radio-opaque marker in the protection zone 43 of the catheter 40 allows for the visualization of the exact placement of the stent or other implantable medical device.

FIG. 2A is an exemplary depiction of a single tungsten-containing radio-opaque marker 51 spanning the length of the protection zone 43. In some embodiments, the single tungsten-containing radio-opaque marker 51 does not span the entire length of the protection zone 43, but is the same length as the implantable medical device.

FIG. 2B is an exemplary depiction of a pair of tungsten-containing radio-opaque markers 52 at the ends of the protection zone 43. In some embodiments, the pair of tungsten-containing radio-opaque markers 52 are directly under the proximal and distal ends of the implantable medical device. In other embodiments, the pair of tungsten-containing radio-opaque markers 52 are immediately proximal and distal to the ends of the implantable medical device.

FIG. 2C is an exemplary depiction of a pair of integrated tantal markers 53 at the ends of the protection zone 43. In some embodiments, the pair of integrated tantal markers 53 are directly under the proximal and distal ends of the implantable medical device. In other embodiments, the pair of integrated tantal markers 53 are immediately proximal and distal to the ends of the implantable medical device.

In another related embodiment, the length of the protection zone 43 is between about 50 mm and about 250 mm. In a further embodiment, the length of the protection zone 43 is between about 100 mm and about 200 mm. In a still further embodiment, the length of the protection zone 43 is about 152 mm. In a particular embodiment, the protection zone 43 has a flexibility index of about 2000-4000 mN in a 3 point bending deflection test. In another embodiment, the protection zone 43 has a flexibility index of about less than 3000 mN in a 3-point bending deflection test. In a further embodiment, the protection zone 43 has a flexibility index of about 2700-3000 mN in a 3 point bending deflection test.

In a particular embodiment, the catheter device 40 further comprises a protective sheath that extends from the delivery device 100 to and covering the implantable medical device emplaced on the protection zone 43. When the catheter has been inserted to the point where the implantable medical device is to be deployed, the first handle 24 of first tubular member is withdrawn towards base handle 12, withdrawing the protective sheath towards the delivery system and exposing the implantable medical device.

In some embodiments, the implantable medical device is a self-expanding stent or other implantable device, wherein drawing back of the sheath allows the device to immediately expand against the walls of the body lumen.

In another particular embodiment, the catheter device 40 comprises a "flexibility" zone 44 immediately proximate to the protection zone 43. The flexibility zone 44 of the catheter is flaccid enough to allow the direction of the tip 41, stabilization zone 42 and protection zone 43 to be easily guided by the externally controlled magnetic field, however is rigid enough to prevent the zone from collapsing or folding as the catheter is being advanced into/through the body lumen.

In a related embodiment, the flexibility zone 44 is between about 50 mm and about 150 mm. In a further embodiment, the length of the flexibility zone 44 is between about 70 mm and about 120 mm. In a still further embodiment, the length of the flexibility zone 44 is about 90 mm. In a particular embodiment, the flexibility zone 44 has a flexibility index of about 2000-4000 mN in a 3 point bending deflection test. In another embodiment, the flexibility zone 44 has a flexibility index of about less than 3500 mN in a 3-point bending deflection test. In a further embodiment, the flexibility zone 44 has a flexibility index of about 3000 mN in a 3 point bending deflection test. In particular embodiments, the flexibility index of the flexibility zone 44 is higher than that of the of the flexibility index of the stabilization zone 42 or the protection zone 43. In some embodiments, the flexibility index of the flexibility zone 44 is within the range of about 100%-110% of the flexibility index of the stabilization zone 42 or the protection zone 43.

In another particular embodiment, the catheter device 40 comprises a "trackability" zone 45 immediately proximate to the flexibility zone 44. The trackability zone 45 is of an intermediate flexibility between that of the more flexible flexibility zone 44 and the more rigid pushability zone 46. In a particular embodiment, the trackability zone 45 has a flexibility index of about 3000-5000 mN in a 3 point bending deflection test. In another embodiment, the trackability zone 45 has a flexibility index of about less than 4500 mN in a 3-point bending deflection test. In a further embodiment, the trackability zone 45 has a flexibility index of about 3900-4100 mN, more particularly of about 4000 mN, in a 3 point bending deflection test. In particular embodiments, the flexibility index of the trackability zone 45 is higher than that of the of the flexibility index of the flexibility zone 44. In some embodiments, the flexibility index of the trackability zone 45 is within the range of about 110%-150% of the flexibility index of the flexibility zone 44. The intermediate rigidity of the trackability zone allows the catheter device 40 to easily track through complex bends in a lumen or vessel without kinking or folding. In some embodiments, a radio-opaque substance is embedded into the trackability zone 45. In another still further embodiment, the trackability zone 45 is coated or painted with a radio-opaque substance.

In a related embodiment, the trackability zone 45 is between about 100 mm and about 300 mm. In a further embodiment, the length of the trackability zone 45 is between about 150 mm and about 250 mm. In a still further embodiment, the length of the trackability zone 45 is about 195 mm.

In certain embodiments, the catheter device 40 comprises a "pushability" zone 46. In one embodiment, the pushability zone 46 is immediately proximate to the trackability zone 45. The pushability zone 46 is a relatively rigid zone of the catheter that allows the practitioner to apply force in order to advance the catheter device 40 into/through the body lumen or vessel. The pushability zone 46 may be made of any biocompatible material with suitable hardness and rigidity for the delivery of the implantable medical device, but is flexible enough to allow the catheter to bend and twist through body lumensor vessels. In particular embodiments the biocompatible material is made of nylon, a polyamide, or polyetheretherketone (PEEK). In some embodiments, the pushability zone is more rigid than the trackability zone 45. In other embodiments, the pushability zone and the trackability zone have about the same rigidity. In a particular embodiment, the pushability zone 46 has a flexibility index of about 4000-7000 mN in a 3 point bending deflection test. In another embodiment, the pushability zone 46 has a flexibility index of about less than 6000 mN in a 3-point bending deflection test. In a further embodiment, the pushability zone 46 has a flexibility index of about 5200-5700 mN in a 3 point bending deflection test, more particularly about 5300 mN. In particular embodiments, the flexibility index of the trackability zone 45 is within about 25% of the flexibility index of the trackability zone 45.

In a related embodiment, the pushability zone 46 is between about 100 mm and about 620 mm. In a further embodiment, the length of the pushability zone 46 is between about 230 mm and about 490 mm. In a still further embodiment, the length of the pushability zone 46 is about 360 mm.

In a separate related embodiment, the pushability zone 46 is between about 500 mm and about 1020 mm. In a further embodiment, the length of the pushability zone 46 is between about 630 mm and about 890 mm. In a still further embodiment, the length of the pushability zone 46 is about 760 mm. In another still further embodiment, the length of the pushability zone 46 is about 767 mm.

In a particular embodiment, the total combined length of the stabilization zone 42, protection zone 43, flexibility zone 44, trackability zone 45 and pushability zone 46 is about 800 mm. In another particular embodiment, the total combined length of the stabilization zone 42, protection zone 43, flexibility zone 44, trackability zone 45 and pushability zone 46 is about 1200 mm. In still another particular embodiment, the total combined length of the stabilization zone 42, protection zone 43, flexibility zone 44, trackability zone 45 and pushability zone 46 is about 1207 mm.

In particular embodiments, the catheter device 40 further comprises transition areas between the stabilization zone 42 and the protection zone 43, between the protection zone 43 and the flexibility zone 44, between the flexibility zone 44 and the trackability zone 45, and/or between the trackability zone 45 and the pushability zone 46. Each transition area is an area of intermediate flexibility between the adjacent zones it resides between, consisting of a gradual mixture of the polymer mixture of one zone into the adjacent zone, or a gradual change in the weave pattern of the polymer from one zone into the adjacent zone.

In another particular embodiment, a radio-opaque substance is coated on or embedded into the stabilization zone 42.

In another particular embodiment, a radio-opaque substance is coated on or embedded into the protection zone 43.

In another particular embodiment, a radio-opaque substance is coated on or embedded into the flexibility zone 44.

In another particular embodiment, a radio-opaque substance is coated on or embedded into the pushability zone 46.

In another particular embodiment, a radio-opaque substance is coated on or embedded into the entire catheter 40.

In a particular embodiment, the catheter device 40 further comprises a "strain relief" area 47 that is proximate to the pushability zone 46 and distal to an instrument for deploying an implantable medical device in a body lumen, such as the delivery device 100 as described herein. Said strain relief area 47 is interposed between the catheter device 40 and a connector unit 48 attached to the instrument for deploying an implantable medical device in a body lumen.

In a particular embodiment, the connector unit 48 comprises a Y-connector that allows the attachment of a fluid reservoir or syringe. Said fluid reservoir or syringe may comprise an opacity enhancing substance that allows visualization of the balloon when it is inflated. In another particular embodiment, said fluid reservoir is emplaced between the connector unit 48 and the delivery device 100. In a further embodiment, the connector unit 48 is attached to the delivery device 100 at distal end 32 of the second tubular member 30.

Figure 3:
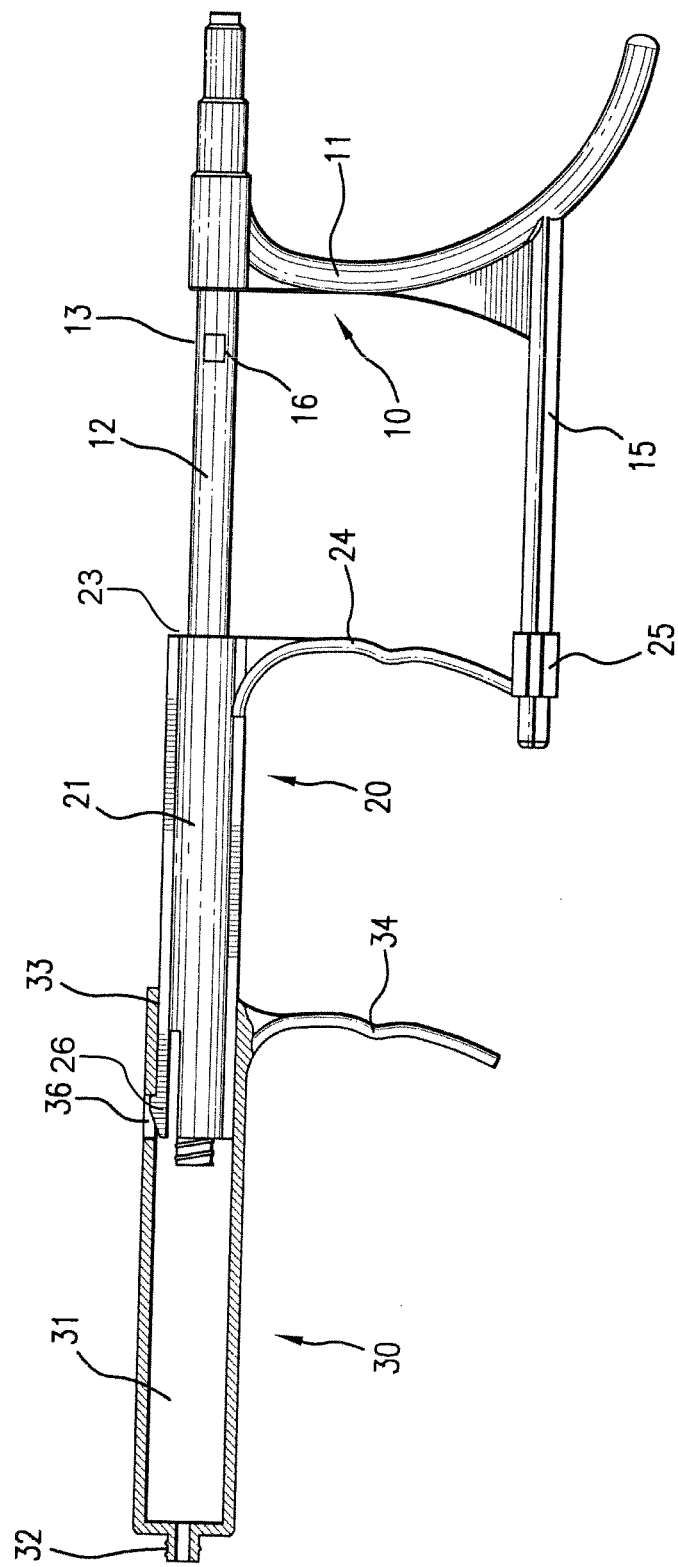
FIG. 3 shows a perspective view of an exemplary delivery device 100 in a pre-deployment configuration.
Figure 4A:
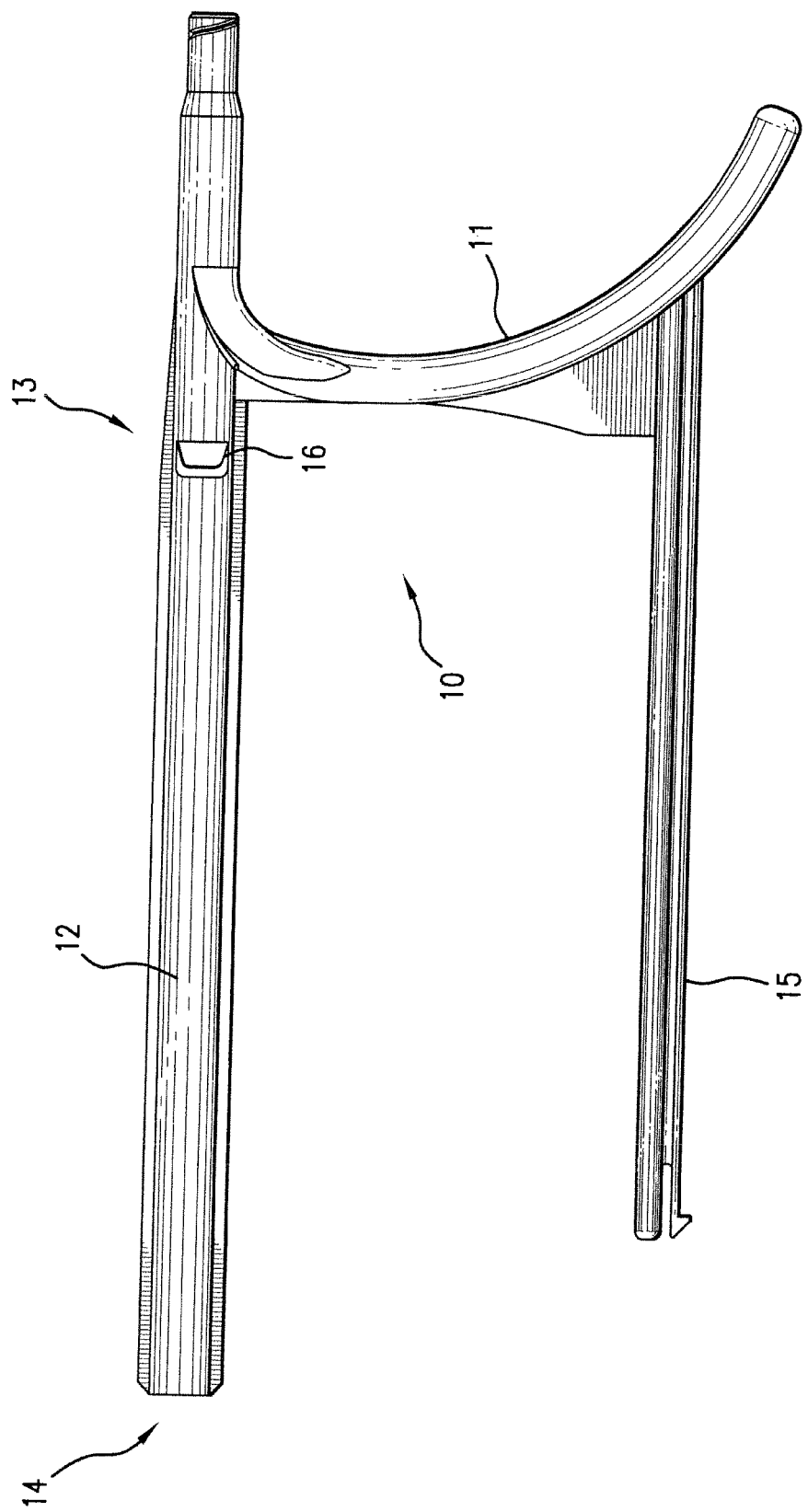
Figure 4B:
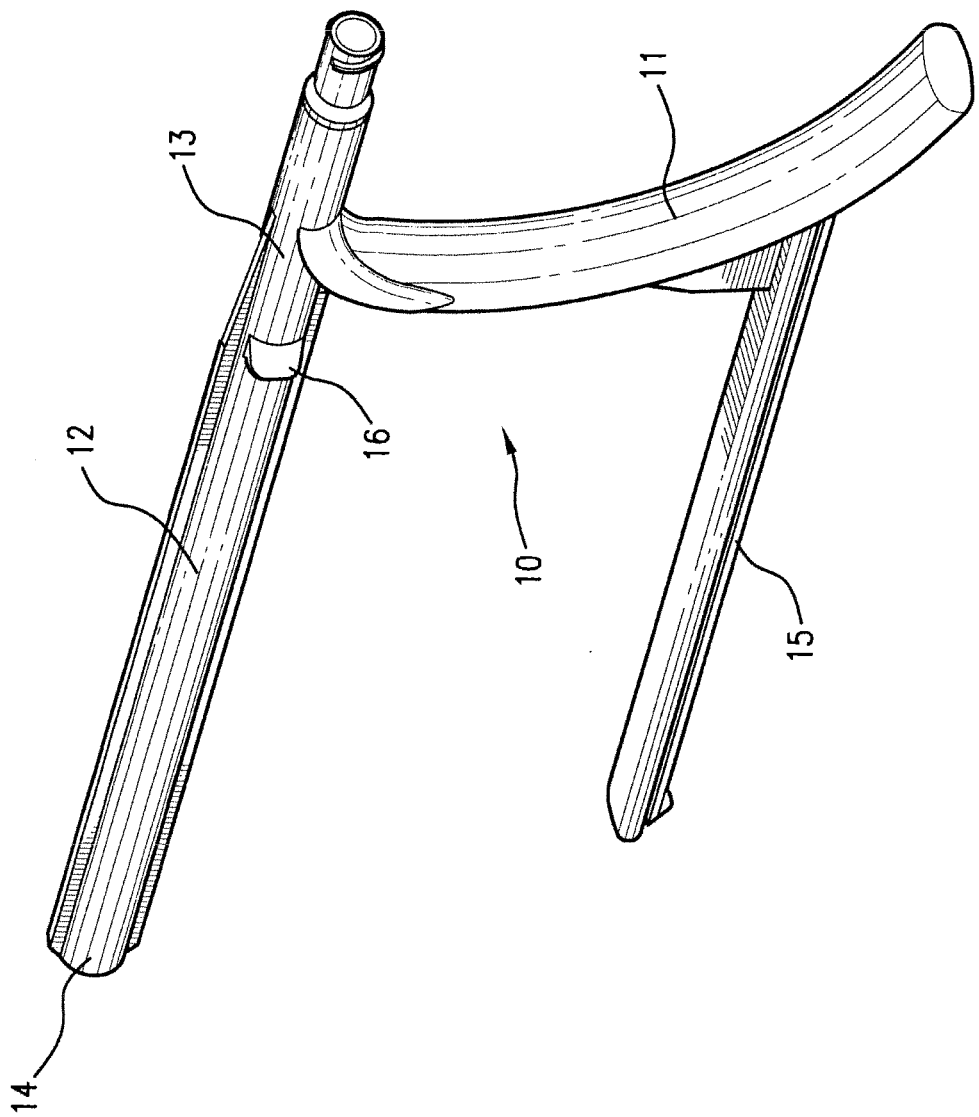

FIGS. 3-9 show more details of the delivery device 100. The delivery device 100 allows the user to install the implantable device with one hand. As shown in FIG. 3, an embodiment of the delivery device 100 contains a base member 10, a first tubular member 20 that fits over the deployment extension 12 and is longitudinally slidable along the deployment extension 12, and a second tubular member 30 that fits over the first tubular member 20 and is longitudinally slidable along the first tubular member 20. As shown in FIGS. 4A-4C, the base member 10 contains a base handle 11 and a deployment extension 12. The deployment extension 12 is a rod-like structure having a proximate end 13, a distal end 14, and a pair of compression stopper 16 (one on each side of the extension 12, see e.g., FIG. 4C) near the proximate end 13 to prevent the device from being over deployed. The proximate end 13 of the deployment extension 12 is removably or permanently connected to the base handle 11. In this embodiment, the base handle 11 further contains a guiding extension 15 that matches with a stabilizing ring on the first tubular member 20 to prevent rotation of the first tubular member 20.

In another embodiment, the base member 10 further contains a scope coupling device so that an optical device, such as an endoscope or a broncoscope, may be attached to the deployment extension 12 to facilitate the deployment of the implantable medical device. In certain embodiments, the scope coupling mechanism allows for the manipulation of the scope (e.g., rotate) with respect to the base member 10 when the scope is coupled to the based member 10. In other embodiments, the base member 10 further contains a guide wire coupling device so that a guide wire may be attached to the deployment extension 12 to facilitate the deployment of the implantable medical device.

Figure 5A:
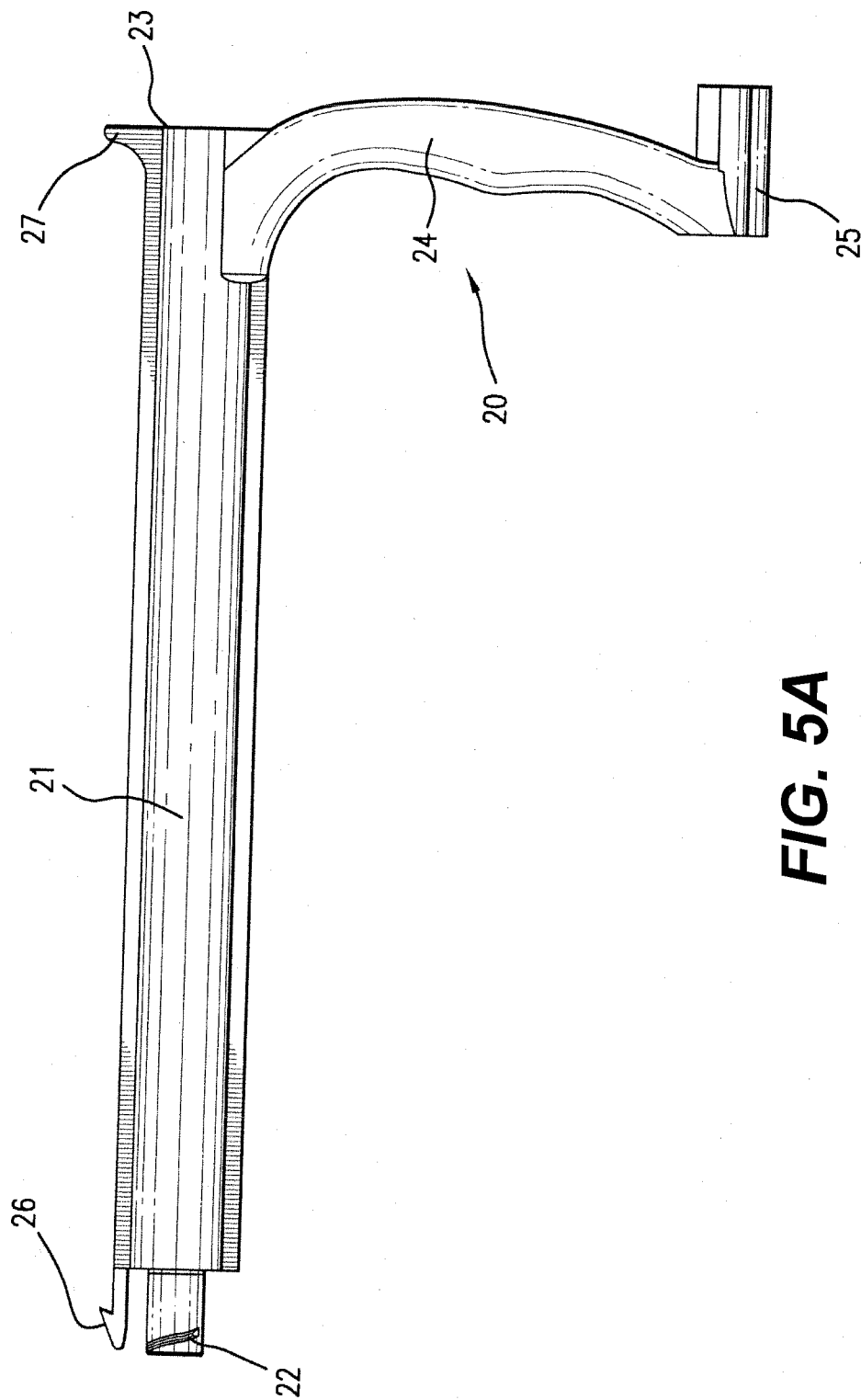
FIGS. 5A-5C are perspective views of the first tubular member of the delivery system 100.
Figure 5B:
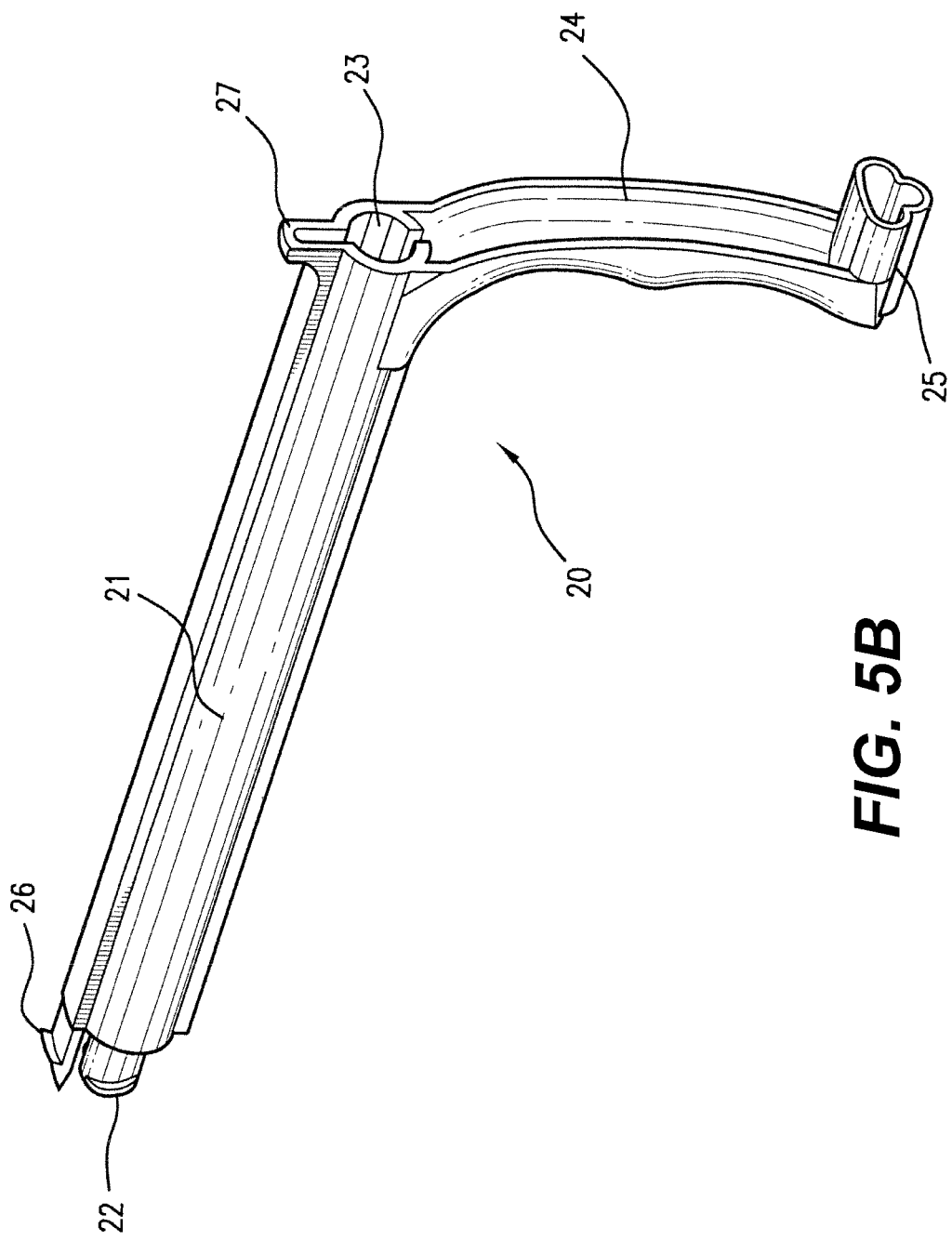
Figure 5C:
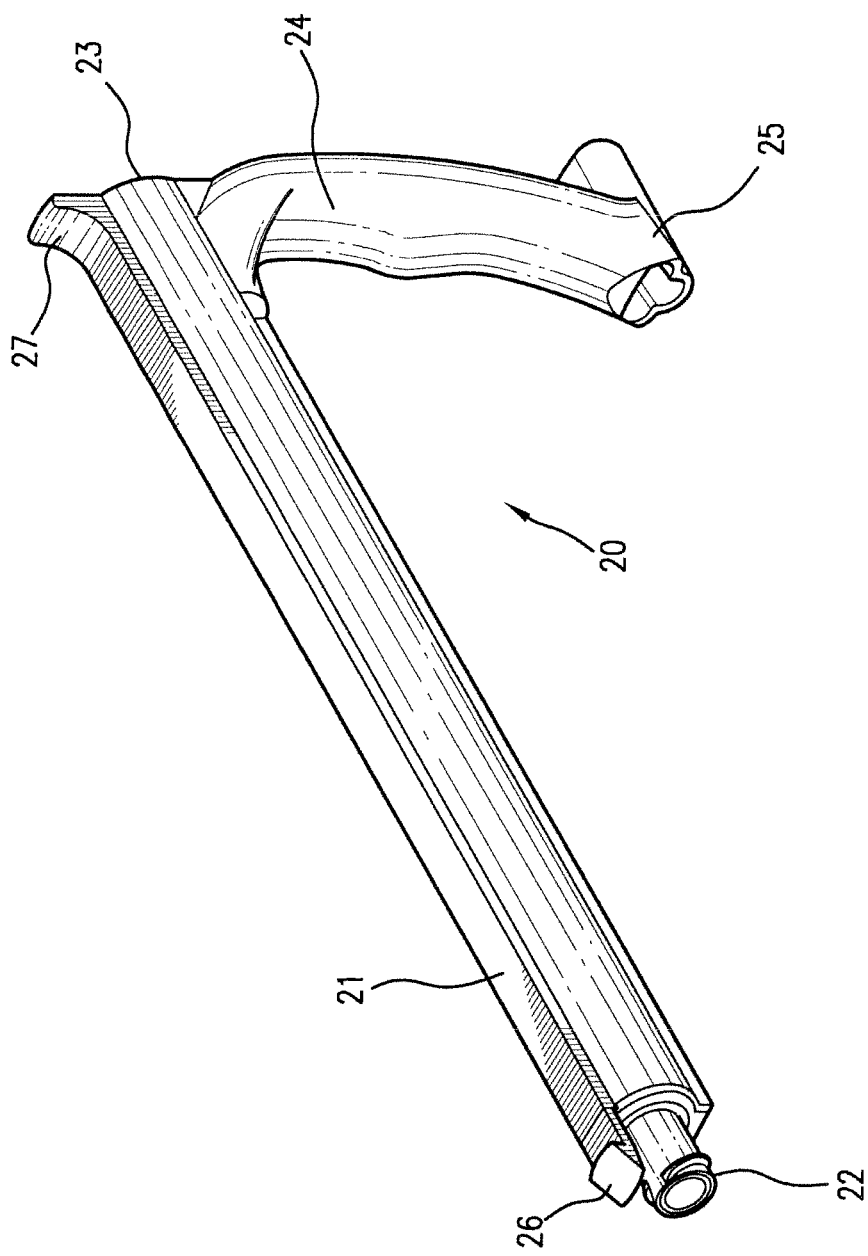
Figure 6A:
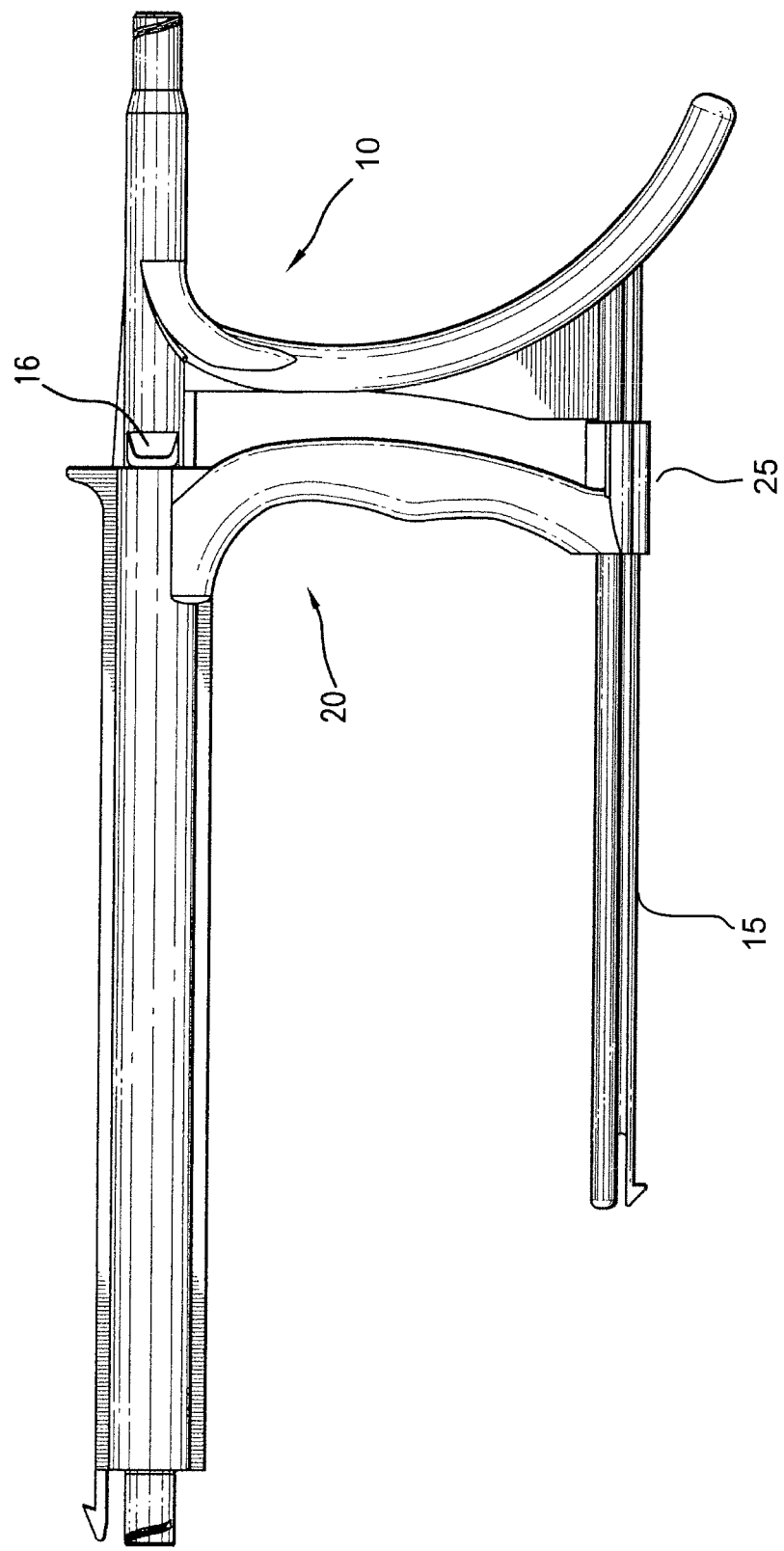
FIGS. 6A-6C are perspective view of the first tubular member in a retracted position.
Figure 6B:
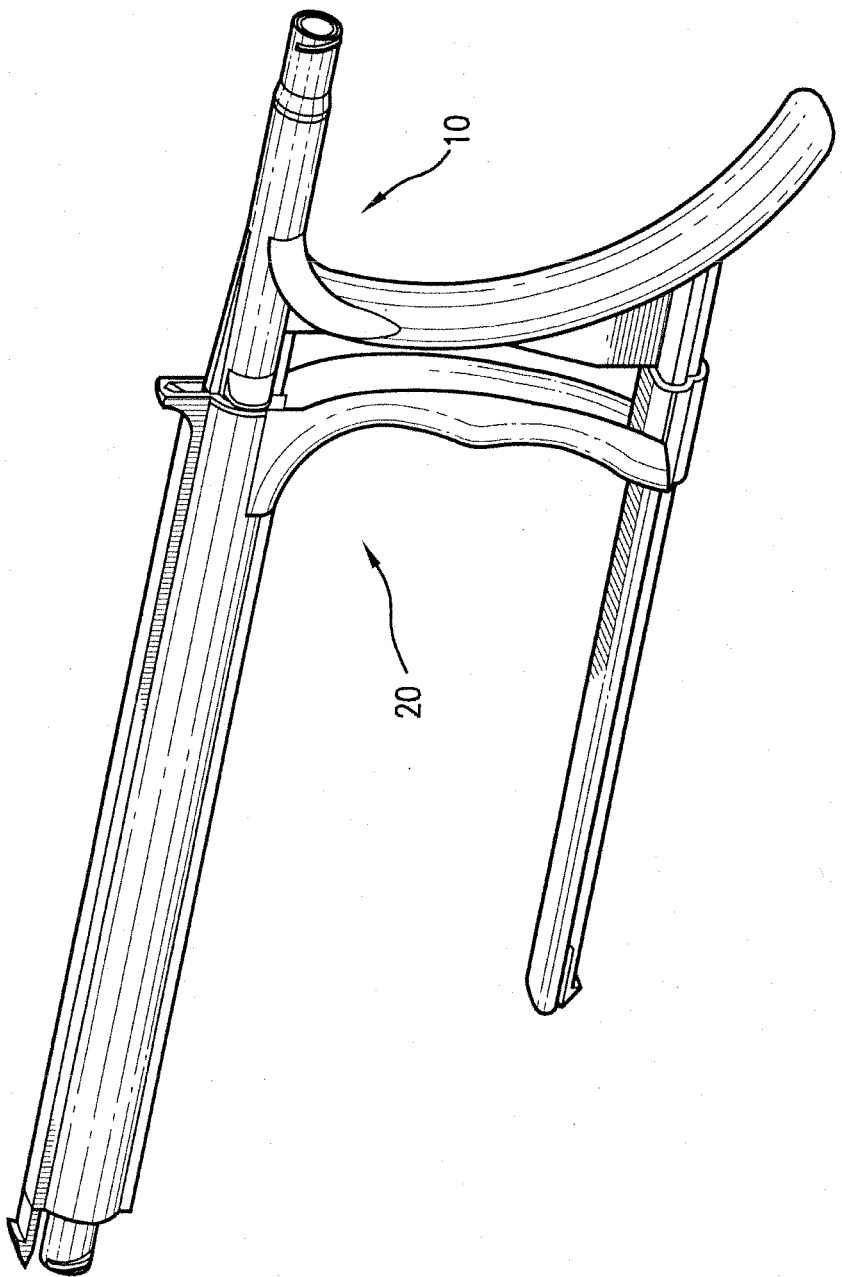
Figure 6C:
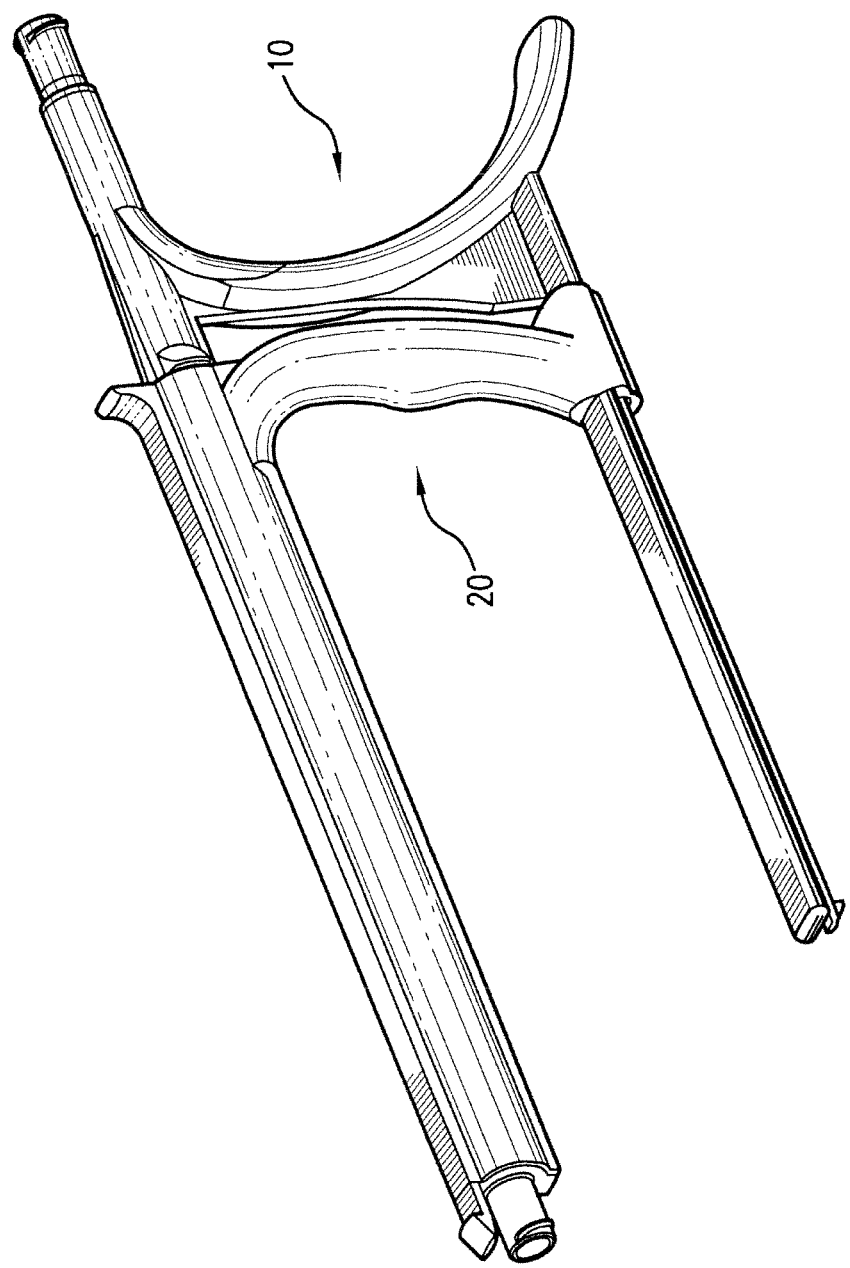

As shown in FIGS. 5A-5C, the first tubular member 20 contains a first tubular body 21 with a distal end 22 and a proximal end 23, and a first handle 24 for controlling movement of the first tubular member 20. The first tubular body 21 has a center lumen with a cross-sectional shape adopted to fit the outside contour of the deployment extension 12 and to slide longitudinally along the deployment extension 12. The first handle 24 further contains a stabilizing ring 25 that fits over the guiding extension 15 of the base handle 12. As shown in FIG. 3, the stabilizing ring 25 slides along the guiding extension 15 of the base handle 11 and prevents rotation of the first tubular member 20 along the central axis of the deployment extension 12. The first tubular member 20 is dissociable from the base member 10 by sliding off from the distal end 14 of the deployment extension 12. FIGS. 6A-6C show the first tubular member 20 in a retracted position with the base member 10.

Figure 7A:
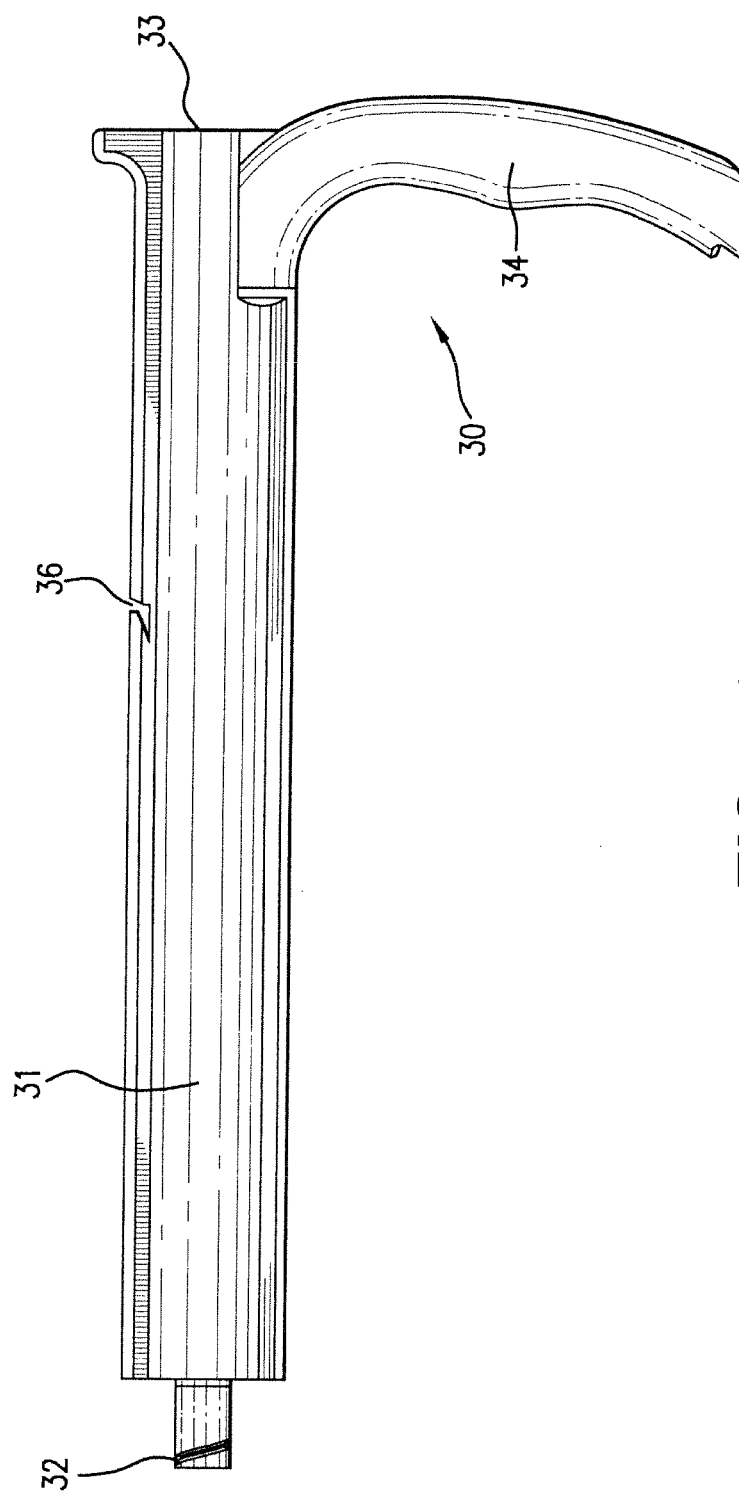
FIGS. 7A-7C are perspective views of the second tubular member of the delivery system 100.
Figure 7B:
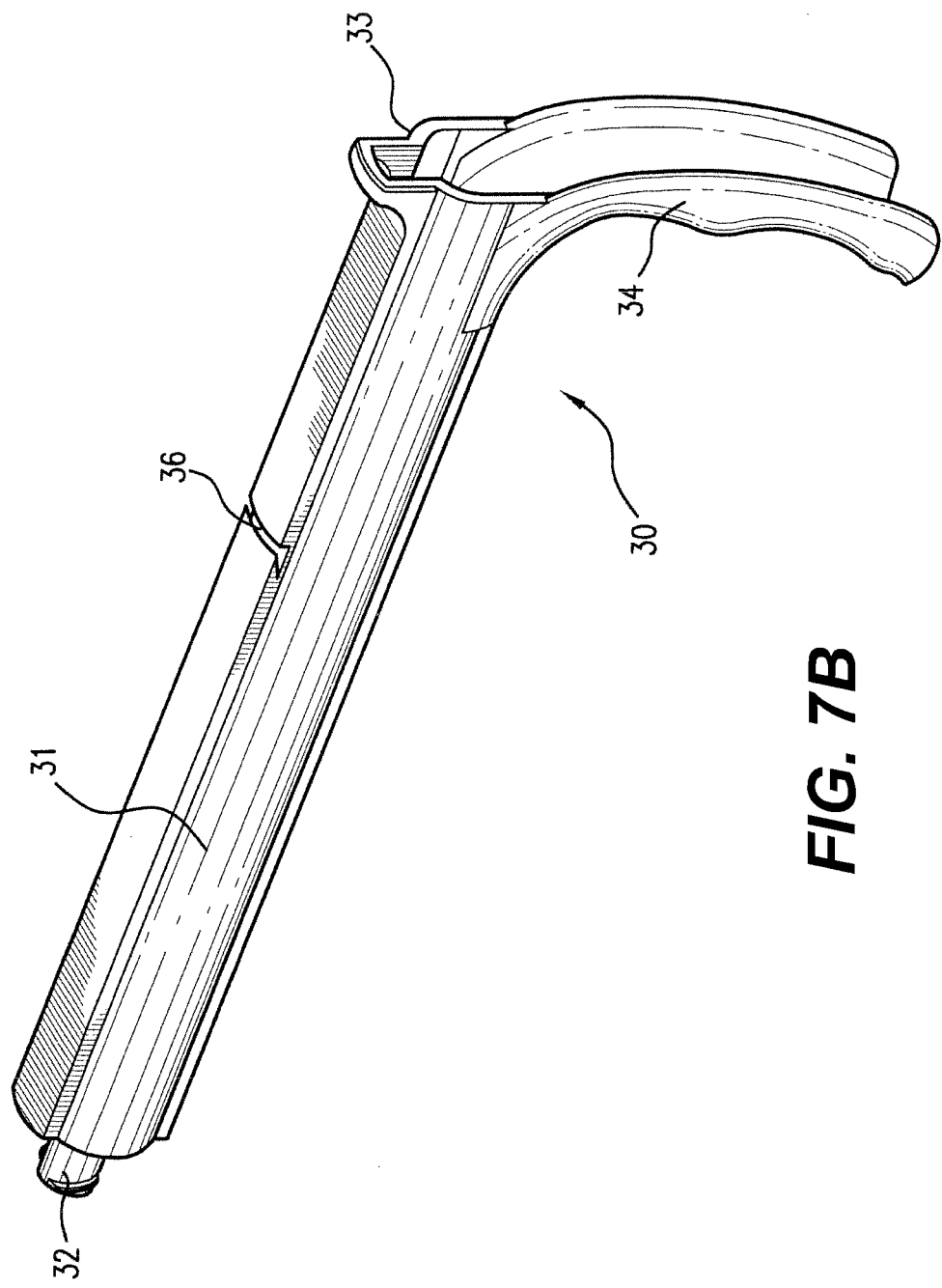
Figure 7C:
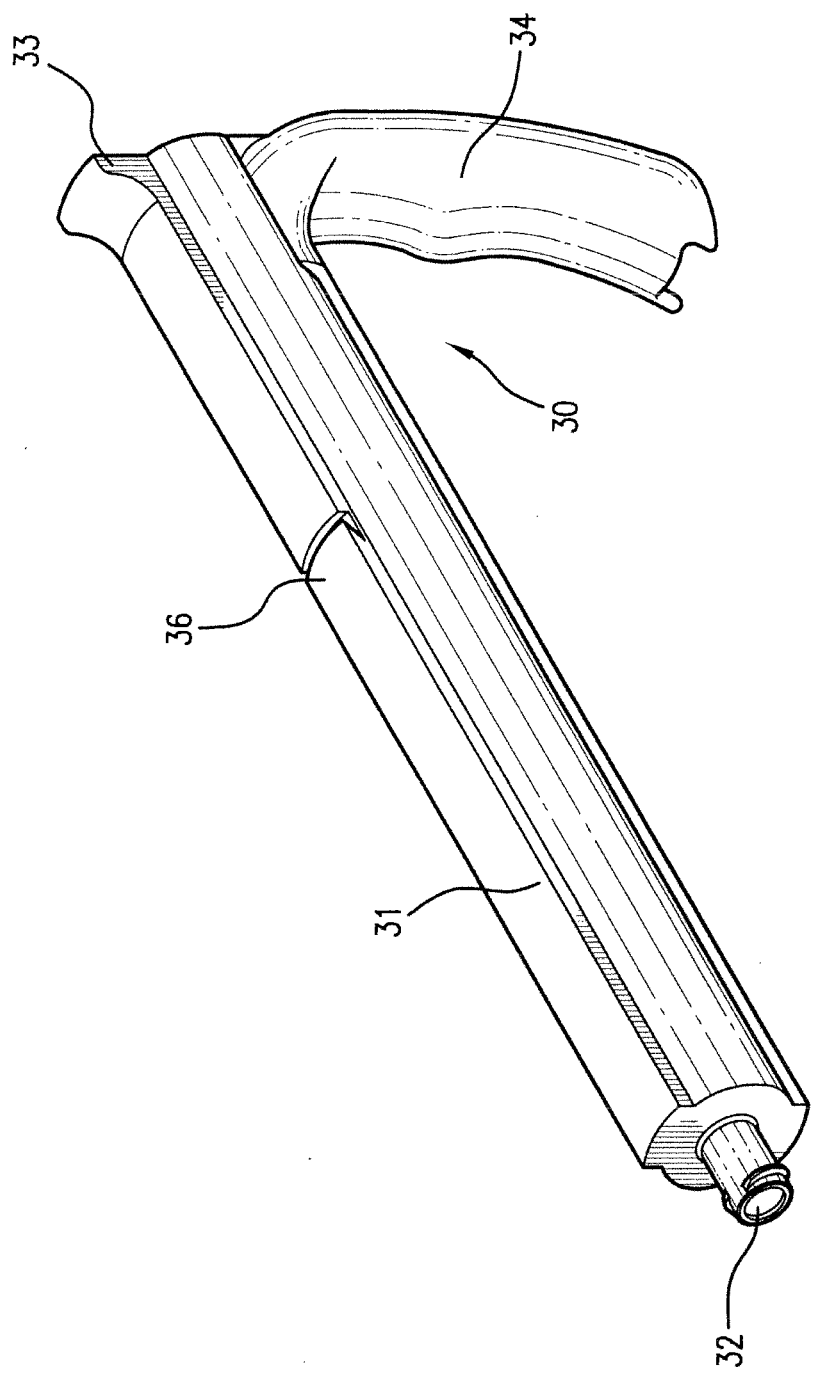
Figure 8A:
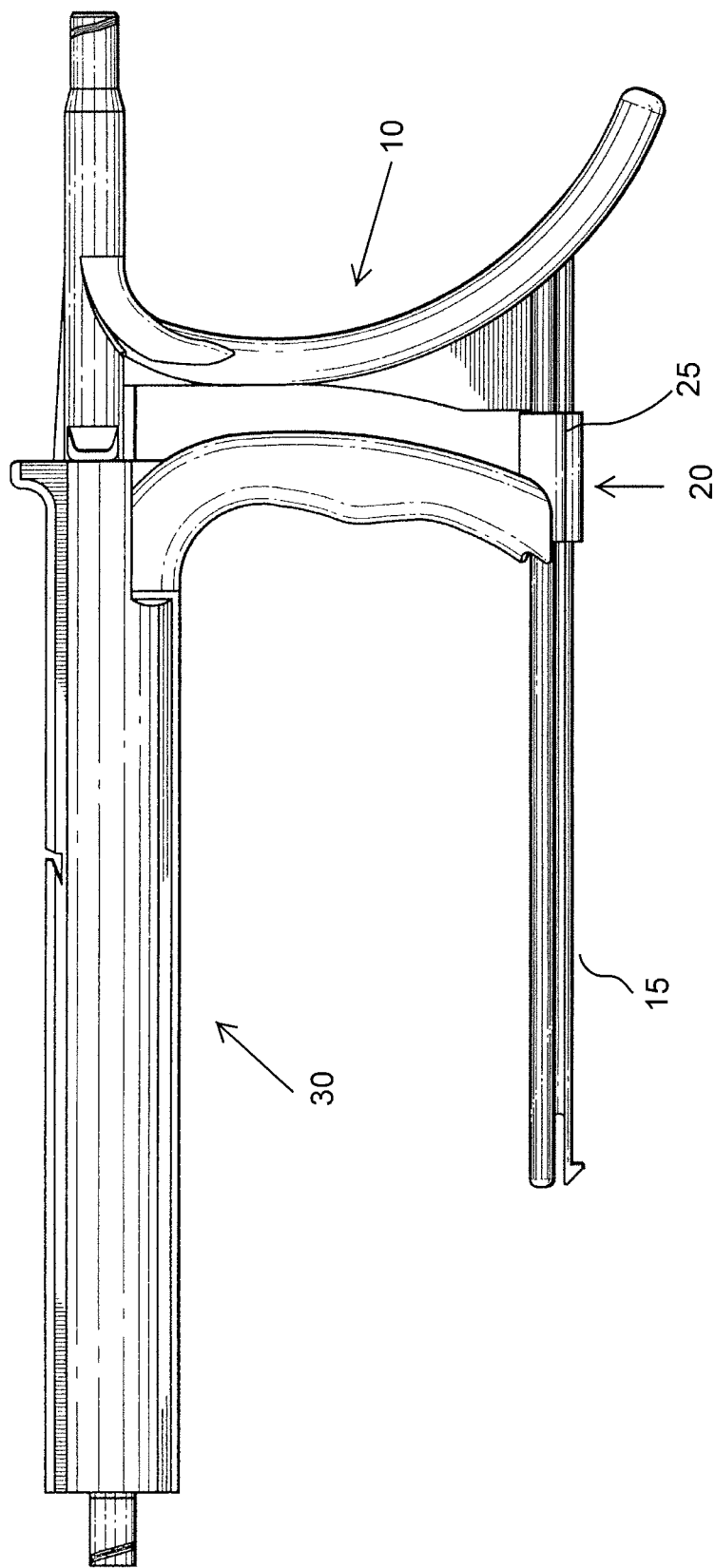
FIGS. 8A-8C are perspective views of the exemplary delivery system 100 in a deployment configuration.
Figure 8B:
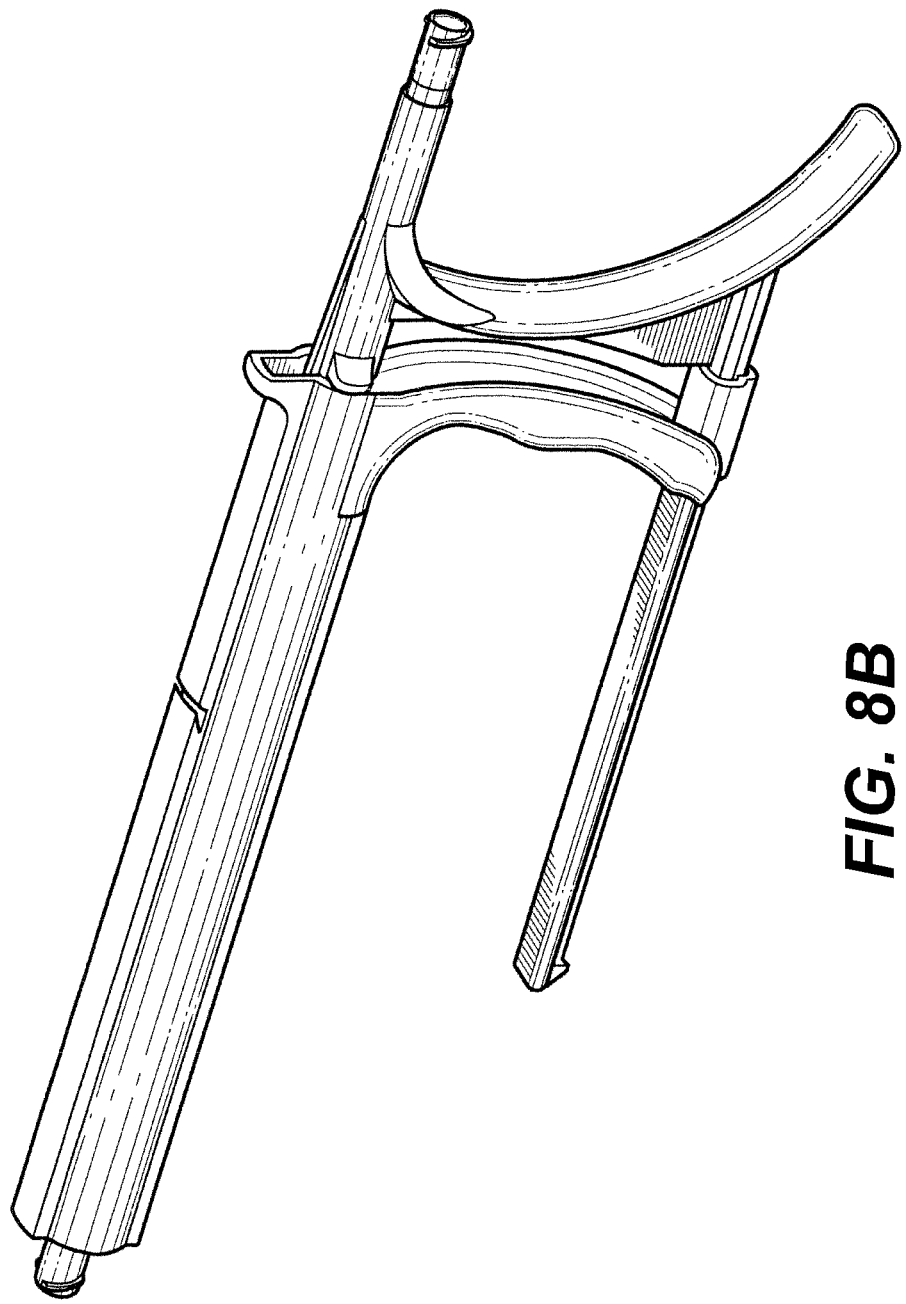
Figure 8C:
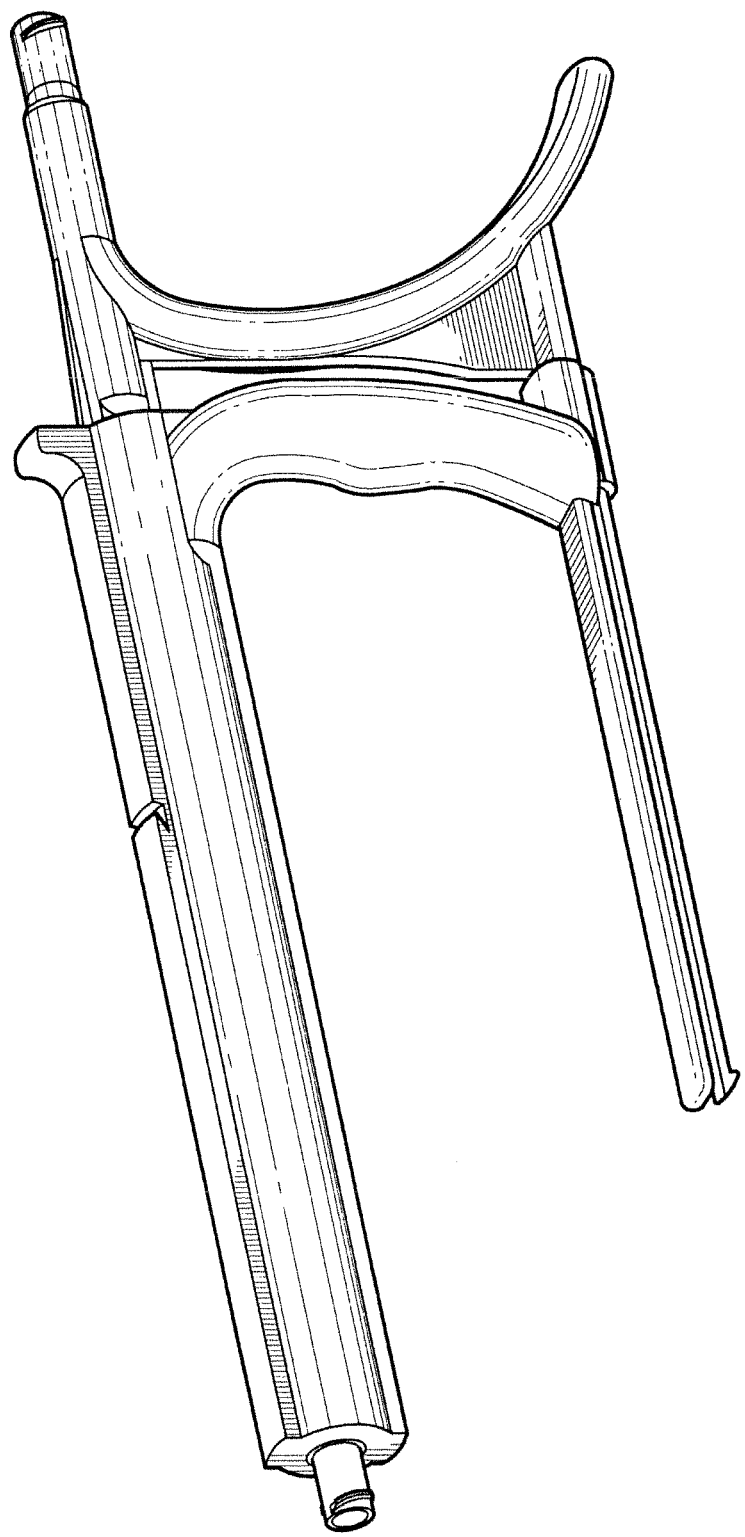

As shown in FIGS. 7A-7C, the second tubular member 30 contains a second tubular body 31 having a distal end 32 and a proximal end 33, and a second handle 34 for controlling movement of the second tubular member 30. The second tubular body 31 has a center lumen with a cross-sectional shape adopted to fit the outside contour of the first tubular body 21 and to slide longitudinally along the first tubular body 21. The second tubular member 30 is dissociable from the first tubular member 20.

As shown in FIGS. 3 and 8A-8C, the first tubular member 20 is connected to the base member 10 through an under-to-over connection. In other words, the first tubular member 20 is connected to the base member 10 by sliding the first tubular body 21 over the deployment extension 12 and the stabilizing ring 25 over the guiding extension 15. Similarly, the second tubular member 30 is also connected to the first tubular member 20 through an under-to-over connection, i.e., by sliding the second tubular body 31 over the first tubular body 21. A person of ordinary skill in the art would understand that the connection can be done in a number of sequences depending on the length of the implantable medical device to be delivered.

In one embodiment, the device 100 also includes an interlocking feature that allows the first tubular member 20 to be locked relative to the second tubular member 30. In one embodiment, the interlocking feature includes a locking tab 26 on the first tubular member 20 and a matching locking hole 33 on the second tubular member 30. As shown in FIG. 3, the locking tab 26 engages with the locking hole 36 to prevent the second tubular member 30 from falling off from the distal end of the first tubular member 20. The tab 26, however, has a beveled front side that allows the second tubular member 30 to slide over the locking tab 26 towards the proximate end 23 of the first tubular body. In another embodiment, the first tubular member 20 further contains a locking guide 27 (see FIGS. 5A-5C). In other embodiments, the device 100 further includes a second interlocking feature that allow the first tubular member 20 to be locked relative to the base member 10.

The distal ends of the deployment extension 12, the first tubular body 21 and the second tubular body 31 are configured to hold, contain or attach to an implantable device. As used herein, the term "implantable device" is broadly interpreted to include stents and other medical devices that can be placed into a body lumen or body cavity. The implantable devices include implantable devices of the Stent Technology System (STS) family developed by ALVEOLUS®, as well as implantable devices developed in accordance with U.S. patent application Ser. Nos. 10/190,770, 10/288,615, and 60/493,402 and International Patent Application Ser. No. PCT/DE02/01244, which are incorporated in their entirety by this reference.

The distal portion of the device can be configured to accommodate variable shafts to allow for ease of manufacturing and interchangeability of varying catheter diameters. In one embodiment, the distal end 14 of the deployment extension 12, the distal end 22 of the first tubular body 21, or the distal end 32 of the second tubular body 31 is configured such that a catheter may be removably attached to the distal end 14, 22 or 32. For example, the catheter may be screwed onto the distal end 14, 22 or 32, or coupled to the device by other conventional means such as a luer, hub, or other standard attachment mechanism.

As would be understand by one skilled in the art, the device 100 is a proportional release system. In certain embodiment, only the base member 10 and the first tubular member 20 are assembled together for deployment of implantable medical devices within a certain length range (e.g., less than about 50 mm). In other embodiment, the base member 10, the first tubular member 20, and the second tubular member 30 are assembled together for deployment of implantable medical devices having a greater length (e.g., about 50 mm to 100 mm). The multi-handle design allows for single-handed placement of the device 100. The parallel guide sheath offered by the deployment extension 12 and the guiding extension 15 provides stability and eliminates rotation of the first tubular member relative to the base member 10. The unique guide sheath also allows index finger rest during deployment. Finger guide for index finger rest for ease of stability and precision placement. In one embodiment, the first tubular member 20 and/or the second tubular member 30 are contoured on one side or on both sides for easy handling with the index finger.

The handles 11, 24 and 34 can be pulled together with a single hand. In one embodiment, the handles can be interlocked into each other in a male- and female connection. For example, the second handle 34 may have a hollow interior to accommodate the first handle 24. Similarly, the first handle 24 may have a hollow interior to accommodate the base handle 11. In one embodiment, both the second handle 34 and the first handle 24 may wrap around base handle 11 when fully compressed. In another embodiment, the second handle 34 is spaced at specific distances from the first handle 24 and the base handle 11 to optimize the closer comfort for the device and improve placement accuracy. The handles may have a beveled or rounded shape to improve ergonomics.

The device 100 may be made of any biocompatible material with suitable hardness and rigidity for the delivery of the implantable medical device. The device should have sufficient flexibility to adapt to anatomical curvatures without loss of ability to push or pull. In one embodiment, the device is made from a plastic material that can be molded to reduce production cost. In other embodiment, the individual parts of the device 100, such as the base member 10, the first tubular member 20 and the second tubular member 30 are interchangeable among different devices 100. The interchangeable parts allow the device 100 to be manufactured in different configurations, such as in a single handle (base member only), double handle (base member+first tubular member), triple handle (base member+first tubular member+second tubular member) or more complex configurations.

Figure 9:
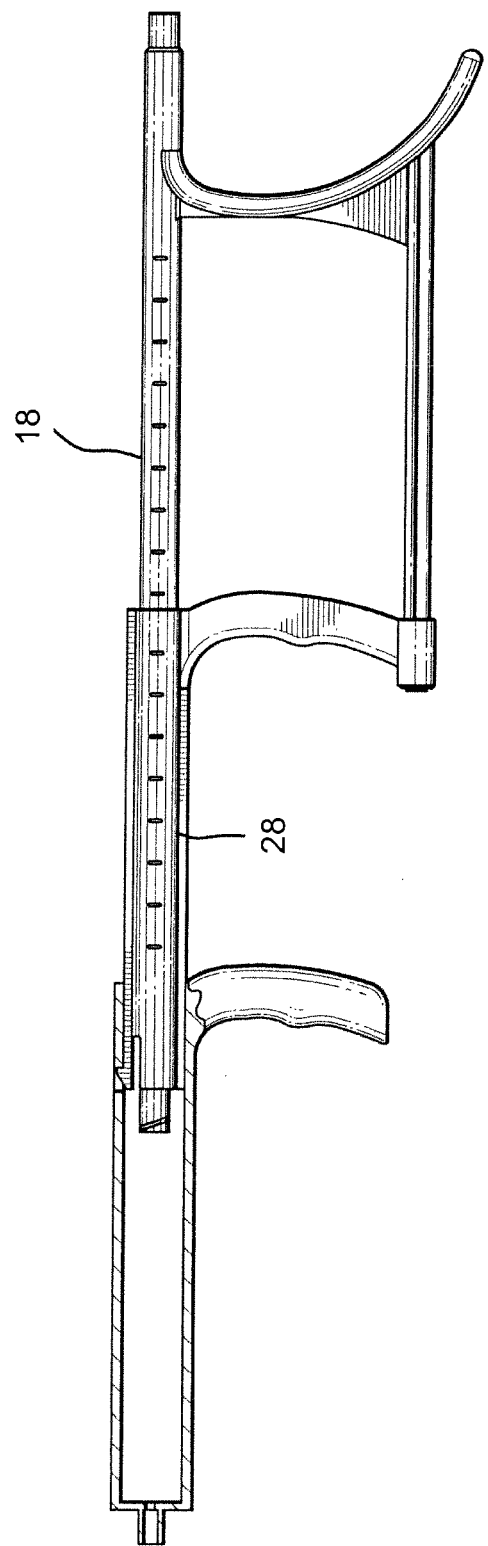
FIG. 9 shows a perspective view of another exemplary delivery system 100 in a pre-deployment configuration.

The diameter and the length of the deployment extension 12, the first tubular body 21 and/or the second tubular body 31, may be designed in compliant with the implantable devices to be delivered and the insertion procedure to be employed. The dimensions of the device must offer enough space for crimped implantable devices. Each individual part of the device should have smooth outer and inner surfaces to provide low friction between the moving parts. In certain embodiments, the deployment extension 12, as well as the first tubular body 21, has external measurement markers 18 and 28 for the determination of retraction distance (FIG. 9).

Also disclosed is a method for delivering an implantable medical device using the delivery device of the present application. The method includes the steps of: attaching the first tubular member 20 to the base member 10 by sliding the first tubular body 21 over the implantable medical device and the deployment extension 12; attaching the second tubular member 30 to the base member 10 by sliding the second tubular body 31 over the first tubular body 21; attaching a proximate end of a catheter to the distal end 32 of the second tubular body 31, wherein an implantable medical device is attached to a distal end of the catheter; advancing the distal end of the catheter into a body lumen; retracting the first tubular member 20 and the second tubular member 30 towards the base member 10 to deploy the medical device. The order of retraction can vary. In one embodiment, the first tubular member 20 is retracted first, followed with the retraction of the second tubular member 30. In another embodiment, the second tubular member 30 is retraced first, followed with the retraction of the first tubular member 20.

The retraction of the first or second tubular member can be easily performed with a single hand using handles 24 or 34. In one embodiment, a user of the device 100 can hold the base handle 11, pull the first handle 24 towards the base handle 11 and hence retract the first tubular member 20. Alternatively, the user may first hold the first handle 24, pull the second handle 34 towards the first handle 24 and hence retract the second tubular member 30. As the second tubular body 31 is retracted over the first tubular body 21, the implantable device is exposed and deployed.

The present invention is further illustrated by the following example which should not be construed as limiting. The contents of all references, patents and published patent applications cited throughout this application, as well as the Figures and Tables, are incorporated herein by reference.

Example 1

Deployment of an Implantable Medical Device

An introducer sheath is inserted in an appropriate site in order to gain access to a vessel or lumen.

A guide wire is inserted through the introducer sheath and advanced through the vessel or lumen to span the area where the implantable medical device is to be deployed.

The tip 41 of the catheter device 40 is advanced onto the guide wire and the catheter device 40 is advanced through the introducer sheath into the vessel or lumen. The catheter device 40 is advanced through the vessel or lumen such that the stabilization zone 42 is advanced beyond the deployment site and the implantable medical device on the protection zone 43 is directly within the deployment site.

The protective sheath is withdrawn by pulling handle 24 toward base handle 11, thereby exposing the implantable medical device at the deployment site.

The implantable medical device is deployed at the site by pulling handle 34 towards handle 24 and base handle 11, thereby inflating the protection zone 43 and expanding the implantable medical device against the walls of the lumen.

Following deployment of the implantable medical device, the catheter device 40 is withdrawn from the vessel or lumen. The guide wire and introducer sheath are removed and the incision at the entry point is sutured.

Example 2

Benefits of the Catheter of the Present Application

Figure 10:
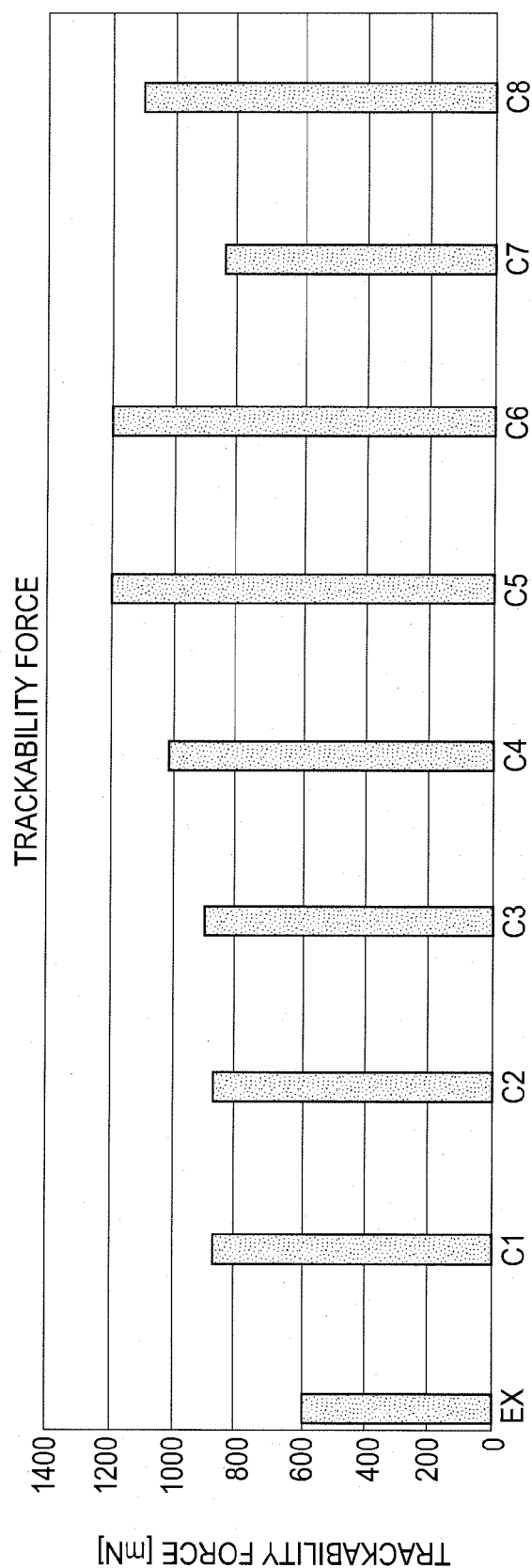
FIG. 10 is a diagram comparing trackability force of the catheter of the present application (EX) to that of other comparable devices (C1-C8).
Figure 11:
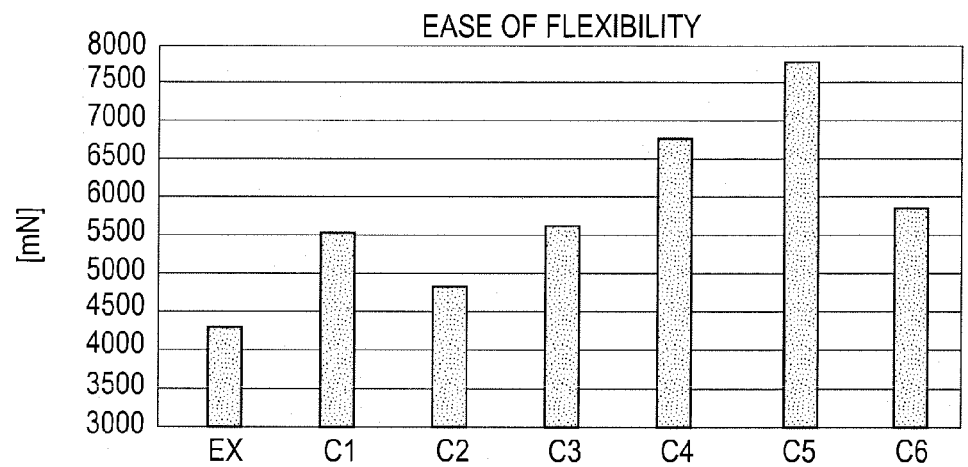
FIG. 11 is a diagram comparing ease of flexibility of the catheter of the present application (EX) to that of other comparable devices (C1-C6).
Figure 12:
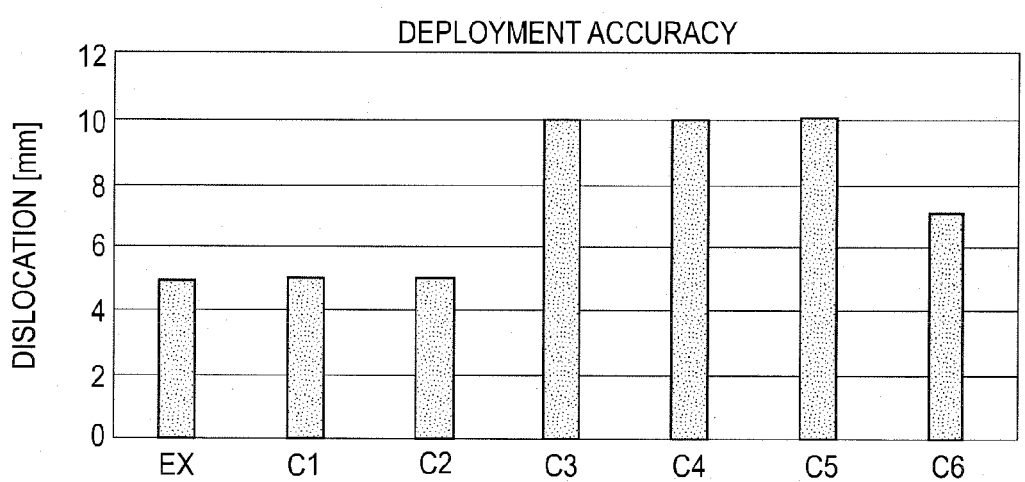
FIG. 12 is a diagram comparing deployment accuracy of the catheter of the present application (EX) to that of comparable devices (C1-C6).

The catheter of the present application were tested against a number of comparable catheter products. As shown in FIGS. 10-12, the catheter of the present application exhibits the best trackability, flexibility and deployment accuracy among the catheters tested.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for deploying an implantable medical device comprising;
    advancing a catheter into a body lumen, the catheter comprises:
        an elongated body having a distal end and a proximate end, the elongated body further comprising:
        a stabilization zone at the distal end;
        a protection zone located between the stabilization zone and the proximate end, wherein the protection zone is adapted to carry an implantable device;
        a flexibility zone located between the protection zone and the proximate end;
        a trackability zone located between the flexibility zone and the proximate end;
        a pushability zone located between the trackability zone and the proximate end;
        a connector at the proximate end for connecting to an advancing device; and
        the implantable medical device affixed to the protection zone;
    attaching the proximal end of the catheter to the advancing device, the advancing device comprising:
        a base member comprising a base handle; and
        a deployment extension having a distal end and a proximate end, the proximate end is connected to the base handle, wherein the distal end of the deployment extension is configured to accommodate variable shafts to allow for interchangeability of varying catheter diameters;
        a first tubular member that fits over the deployment extension and is longitudinally slidable over the deployment extension, the first tubular member comprising:
            a first tubular body with a distal end and a proximal end; and
            a first handle for controlling movement of the first tubular member, the first handle disposed between the first tubular body and the guiding extension; and
        a second tubular member that fits over the first tubular member and is longitudinally slidable over the first tubular member, the second tubular member comprising:
            a second tubular body with a distal end and a proximal end; and
            a second handle for controlling movement of the second tubular member,
            wherein the first handle is located between the base handle and the second handle and
            wherein the distal ends of the deployment extension, the first tubular body, and the second tubular body are adapted to deploy an implantable medical device, and
    retracting the first tubular member and the second tubular member towards the base member to deploy the implantable medical device in the body lumen.

2. The method of claim 1, wherein the implantable medical device is a stent.

3. The method of claim 1, further comprising attaching a viewing device to the base member.

4. The method of claim 3, wherein the viewing device is an endoscope.

5. The method of claim 1, wherein the body lumen is a blood vessel or a bile duct.

6. The method of claim 1, wherein the protection zone of the catheter comprises an inflatable balloon for deploying the implantable medical device.

7. The method of claim 1, wherein the tractability zone of the catheter is coated with or comprises an embedded radio-opaque substance.

8. The method of claim 1, wherein the stabilization zone of the catheter is coated with or comprises an embedded radio-opaque substance.

9. The method of claim 1, wherein the protection zone of the catheter is coated with or comprises an embedded radio-opaque substance.

10. The method of claim 1, wherein the flexibility zone of the catheter is coated with or comprises an embedded radio-opaque substance.

11. The method of claim 1, wherein the pushability zone of the catheter is coated with or comprises an embedded radio-opaque substance.

12. The method of claim 1, wherein the catheter further comprises a transition area resided between two adjacent zones of different flexibility, wherein the transition area has a flexibility that is intermediate between the flexibilities of the two zones.

13. The method of claim 1, wherein the catheter further comprises a strain relief area between the pushability zone and the connector.

14. The method of claim 1, wherein the stabilization zone and the protection zone of the catheter have a flexibility index of less than 3000 mN.

15. The method of claim 1, wherein the flexibility zone of the catheter has a flexibility index of less than 3500 mN.

16. The method of claim 1, wherein the trackability zone has a flexibility index of less than 4500 mN.

17. The method of claim 1, wherein the pushability zone of the catheter has a flexibility index of less than 6000 mN.

18. The method of claim 1, wherein the stabilization zone and the protection zone of the catheter have a flexibility index of less than 3000 mN, the flexibility zone of the catheter has a flexibility index of less than 3500 mN, the trackability zone of the catheter has a flexibility index of less than 4500 mN, and the pushability zone of the catheter has a flexibility index of less than 6000 mN.

19. The method of claim 1, wherein the diameters of the zones of the catheter are the same as one another.

20. The method of claim 1, wherein the diameters of the zones of the catheter are different from one another.

21. The method of claim 1, wherein the advancing device comprises a guiding extension connected to the base handle and extending in a direction parallel to the deployment extension, and wherein the first handle comprises a stabilizing ring fitting over the guiding extension and longitudinally slidable thereover such that movement of the first tubular member is controlled and rotation of the first tubular member relative to the base member is prevented.

* * * * *